US011008362B2

(12) United States Patent
Lohman et al.

(10) Patent No.: US 11,008,362 B2
(45) Date of Patent: May 18, 2021

(54) MALONYL-COENZYME A MIMICS AS FATTY ACID SYNTHASE INHIBITORS AND METHODS OF USE

(71) Applicant: Purdue Research Foundation, West Lafayette, IN (US)

(72) Inventors: Jeremy R. Lohman, West Lafayette, IN (US); Lee M. Stunkard, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/432,147

(22) Filed: Jun. 5, 2019

(65) Prior Publication Data
US 2019/0375780 A1 Dec. 12, 2019

Related U.S. Application Data

(60) Provisional application No. 62/681,154, filed on Jun. 6, 2018.

(51) Int. Cl.
| | |
|---|---|
| *C07H 19/207* | (2006.01) |
| *C07F 9/09* | (2006.01) |
| *C07C 233/13* | (2006.01) |
| *C07C 309/21* | (2006.01) |

(52) U.S. Cl.
CPC ......... *C07H 19/207* (2013.01); *C07C 233/13* (2013.01); *C07C 309/21* (2013.01); *C07F 9/091* (2013.01)

(58) Field of Classification Search
CPC .... C07H 19/207; C07C 233/13; C07C 309/21
See application file for complete search history.

(56) References Cited

PUBLICATIONS

Martin (Journal of the American Chemical Society, 1994, 116, 4660-4668).*
Kulkarni, R., et al., Discovering Targets of Non-enzymatic Acylation by Thioester Reactivity Profiling. Cell Chem Biol, 24 (2), pp. 231-242, 2017.
Benning, M., et al., "New reactions in the crotonase superfamily: structure of methylmalonyl CoA decarboxylase from *Escherichia coli*", Biochemistry 2000, 39 (16), pp. 4630-4639, 2000.
Ellis, B., et al., "An Oxetane-Based Polyketide Surrogate To Probe Substrate Binding in a Polyketide Synthase", Journal of the American Chemical Society, 140, pp. 4961-4964, 2018.
Ballatore, C., et al., "Carboxylic acid (bio)isosteres in drug design", ChemMedChem, 8 (3), pp. 385-395, 2013.
Lassalas, P., et al., "Structure Property Relationships of Carboxylic Acid Isosteres", Journal of medicinal chemistry, 59, pp. 3183-3203, 2016.
Kluger, R., "Decarboxylation, CO2 and the reversion problem", Acc Chem Res, 48, pp. 2843-2849., 2015.
Haller, T., et al., "Discovering new enzymes and metabolic pathways: conversion of succinate to propionate by *Escherichia coli*", Biochemistry, 39 (16), pp. 4622-4629, 2000.
Lu, J., et al., "Novel form of the Michaelis-Menten equation that enables accurate estimation of (kcat/KM)*KI with just two rate measurements; utility in directed evolution", Protein engineering, design & selection, 30 (5), pp. 395-399, 2017.
Brinster, S., et al., "Type II fatty acid synthesis is not a suitable antibiotic target for Gram-positive pathogens", Nature, 458 (7234), pp. 83-86, 2009.
Balemans, W., et al., "Essentiality of FASII pathway for *Staphylococcus aureus*", Nature, 463 (7279), pp. 5, 2010.
Yao, J., et al., "Type II fatty acid synthesis is essential for the replication of Chlamydia trachomatis", The Journal of biological chemistry, 289, (32), pp. 22365-22376, 2014.
Parsons, J., et al., "Is bacterial fatty acid synthesis a valid target for antibacterial drug discovery?", Current opinion in microbiology, 14, (5), pp. 544-549, 2011.
Yao, J., et al., "How bacterial pathogens eat host lipids: implications for the development of fatty acid synthesis therapeutics", The Journal of biological chemistry, 290, (10), pp. 5940-5946, 2015.
Currie, E., et al., Cellular fatty acid metabolism and cancer, Cell Metab., 18, (2), pp. 153-161, 2013.
Luo, X., et al., "Emerging roles of lipid metabolism in cancer metastasis", Mol Cancer., 16, (1), pp. 10, 2017.
Gonzalez-Guerrico, A., et al., "Suppression of endogenous lipogenesis induces reversion of the malignant phenotype and normalized differentiation in breast cancer", Oncotarget, 7(44), pp. 71151-71168, 2016.
Finzel, K., et al., "Using modern tools to probe the structure-function relationship of fatty acid synthases", Chembiochem, 16,(4), pp. 528-547, 2015.
Rudolf, J., et al., "Platensimycin and platencin: Inspirations for chemistry, biology, enzymology, and medicine", Biochemical Pharmacology, 133, pp. 139-151, 2017.
Wu, M., et al., "Antidiabetic and antisteatotic effects of the selective fatty acid synthase (FAS) inhibitor platensimycin in mouse models of diabetes", Proceedings of the National Academy of Sciences of the United States of America, 108 (13), pp. 5378-5383, 2011.

* cited by examiner

*Primary Examiner* — Pancham Bakshi
(74) *Attorney, Agent, or Firm* — Purdue Research Foundation; Liang Zeng Yan

(57) ABSTRACT

The present disclosure generally relates to novel compounds as a fatty acid synthase inhibitor useful for the treatment of infection diseases, cancers, or metabolic diseases that malfunction of fatty acid synthase is involved. In particular this present invention directs to malonyl-coenzyme A (CoA) mimetics and methods of use thereof. The invention described herein also pertains to pharmaceutical compositions and methods for treating diseases in mammals using compounds disclosed herein.

10 Claims, 2 Drawing Sheets

MALONYL-COENZYME A MIMICS AS FATTY ACID SYNTHASE INHIBITORS AND METHODS OF USE

CROSS REFERENCE TO RELATED APPLICATIONS

This present patent application relates to and claims the priority benefit of U.S. Provisional Application Ser. No. 62/681,154, filed Jun. 6, 2018, the content of which is hereby incorporated herein by reference in its entirety.

TECHNICAL FIELD

The present disclosure generally relates to novel compounds as a fatty acid synthase inhibitor useful for the treatment of infection diseases, cancers, or metabolic diseases that malfunction of fatty acid synthase is involved. In particular this present invention directs to malonyl-coenzyme A (CoA) mimetics and methods of use thereof. The invention described herein also pertains to pharmaceutical compositions and methods for treating diseases in mammals using compounds disclosed herein.

BACKGROUND AND SUMMARY

This section introduces aspects that may help facilitate a better understanding of the disclosure. Accordingly, these statements are to be read in this light and are not to be understood as admissions about what is or is not prior art.

Inhibitors of fatty acid biosynthetic enzymes are candidates for the treatment of a variety of human diseases, including multidrug resistant microbe infections, cancer, and obesity related disease. Fatty acid synthases (FAS) are attractive drug targets because their protein architectures differ between versions found in bacteria, fungi and humans. Specifically, an acyl carrier protein (ACP) or guides thioester-linked substrates from active site to active site and has protein-protein interactions that differ between organisms. Since the FAS enzymes of various organisms and organelles use the same catalytic mechanisms, a promising route to drug discovery is linking a potent mechanism-based inhibitor with a fragment specific for the protein-protein surface of a particular organism's FAS. Our focus is on ketosynthase (KS) enzymes of FAS. KS carry out the committed irreversible formation of carbon-carbon bonds in a two-step reaction. Previously developed inhibitors that target each step function both in vitro and in vivo. However, these inhibitors have not made it into the clinic due to a lack of target specificity. Structures of KS bound to these inhibitors provide limited or confusing insight into the catalytic details and mechanism. The inherent reactivity of the KS with the substrates prevents capture of complexes, obscuring structural characterization of the catalytic mechanism, and impeding rational drug design. Thus, there is a critical need to elucidate catalytic details and organism-specific KS-ACP biophysical interactions to enable design of inhibitors with value to medicine.

Fatty acid synthase (FAS) generate fatty acids for membrane biosynthesis in all forms of life and triglycerides as energy storage in humans. As such, bacterial FAS are a target for the development of new antibiotics to overcome the rising problem of antibacterial drug resistance (Yao J, et al., *Biochimica et Biophysica Acta* 2017, 1862, 1300-1309). The validity of bacterial FAS as a drug target has been questioned (Brinster S, et al. *Nature* 2009, 458(7234), 83-86). For a few bacteria, FAS gene deletions can be complemented by supplementing in media or serum with fatty acids. However, recent reports clearly establish that FAS is obligatory for most bacterial pathogens (Balemans W, et al., *Nature* 2010, 463(7279), E3; Yao J, et al., *J. Biol. Chem.* 2015, 290(10), 5940-5946). Human cytosolic FAS is upregulated in many tumor types and plays a significant role in cancer cell proliferation (Luo X, et al., *Mol. Cancer* 2017, 16(1), 76). Although the mechanisms of cancer reduction by FAS inhibition are still under investigation, human FAS is an established target for the development of anti-cancer therapeutics (Gonzalez-Guerrico A M, et al., *Oncotarget* 2016, 7(44), 71151-71168). The accumulation of triglycerides produced by FAS can lead to obesity, and is associated with diabetes and cardiovascular diseases (Angeles T S, et al, *Expert Opin Drug Discov.* 2016, 11(12), 1187-1199). The drug orlistat was developed to treat obesity, yet it is only modestly effective. Nevertheless, orlistat establishes FAS as a valid obesity target (Pemble C W, et al., *Nat. Structural & Mol. Biol.* 2007, 14(8), 704-709). Taken together, fatty acid biosynthesis lies at a nexus of human disease, for which new inhibitors can have a significant impact.

FAS can be inhibited at a number of its many enzyme activities; acyltransferase, thioesterase, ketosynthase (KS), ketoreductase, dehydratase, or enoylreductase (Finzel K, et al, *Eur. J. Chem. Biol.* 2015, 16(4), 528-547). Whichever active site is targeted, an effective inhibitor should discriminate between the host, pathogen, microbiome, and between the different versions of FAS within humans. FAS are broadly characterized into two types. Type I FAS consists of a single polypeptide containing all enzymatic activities and are found in the cytoplasm of humans. Fungal type I FAS consists of two polypeptides rather than one. Type II FAS enzymes are expressed individually and provide fatty acids for bacteria but are also found in human mitochondria. However, another type is found in the endoplasmic reticulum of humans, that is relatively unstudied due to membrane association. A number of natural product derived FAS inhibitors target the KS. However, most of these are indiscriminate and inhibit multiple FAS types. The fungus derived cerulenin is very broad spectrum and inhibits the KS of most FAS including human, which was invaluable in establishing a role for FAS in cancer. Platencin and platencimycin were discovered as antibacterial agents, but later shown to accumulate in the liver of mice leading to weight loss, suggesting inhibition of mammalian type I FAS KS (Rudolf J D, et al., *Biochemical Pharmacology* 2017, 133, 139-151; Wu M, et al., *PNAS USA* 2011, 108(13), 5378-5383). Thiolactomycin was discovered over 20 years ago as an antimycobacterial, yet it too has not made it into the clinic.

Here we disclose the synthesis of series analogs of malonyl-coenzyme A and captured them in enzyme active sites, and determined their inhibitory activity against *Escherichia coli* fatty acid biosynthetic enzymes. These analogs may also have inhibitory activity towards cancer cell proliferation and work as a potential treatment for many diseases involving fatty acid biosynthetic enzymes, including many cancers, cardiovascular diseases, infection diseases, obesity, and diabetes.

DETAILED DESCRIPTION

Figure 1:
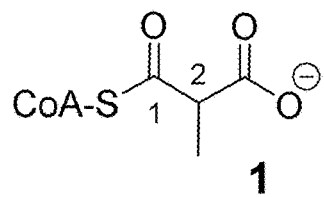
FIG. 1 depicts our methylmalonyl-CoA analogs 4-9 disclosed herein compared to the previously used substrate compound (1), thioether (2) and oxetane (3). CoA here refers to coenzyme A, or CoA analog with the thiol replaced by a hydroxyl or amine. Phosphopantetheine moiety is abbreviated ppant.
Figure 1:
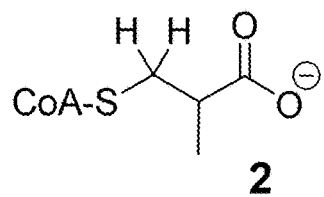
Figure 1:
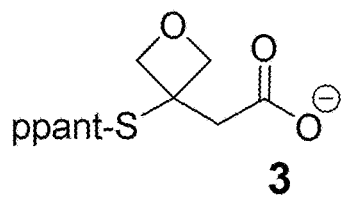
Figure 1:
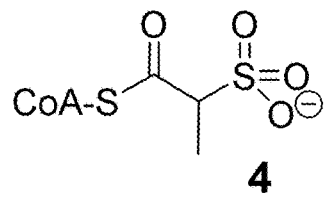
Figure 1:
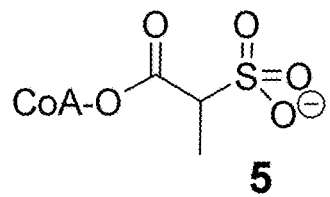
Figure 1:
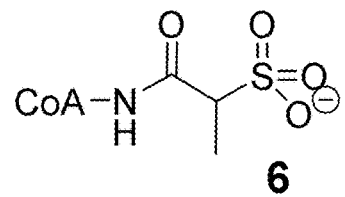
Figure 1:
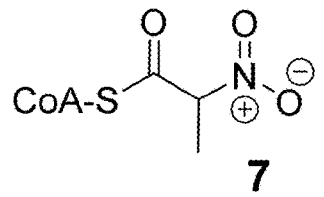
Figure 1:
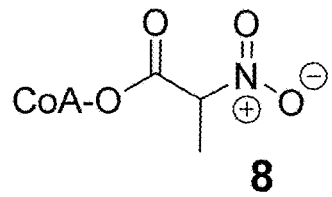
Figure 1:
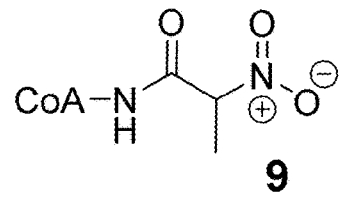

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C (CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art, Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, the invention is related to a compound of formula (I)

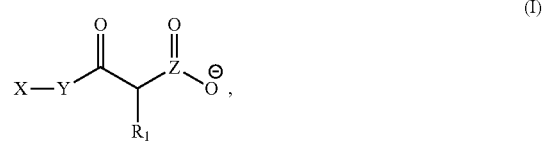

or a pharmaceutically acceptable salt, hydrate, or solvate thereof, wherein
X is co-enzyme A (CoA).

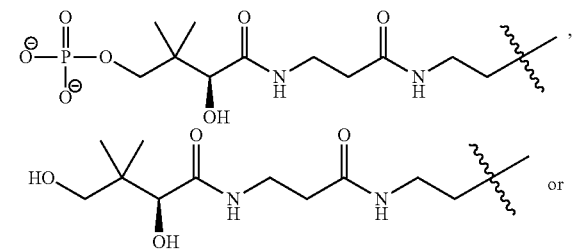

-continued

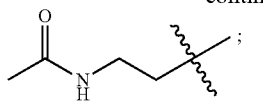

Y is methylene (—CH$_2$—), S, SO, NR, NH, or O;
Z is N$^+$, S or SO; and
R$^1$ is hydrogen, an alkyl, alkenyl, alkynyl, heteroalkyl, heteroalkenyl, heteroalkynyl, cycloalkyl, heterocyloalkyl, cycloalkenyl, heterocycloakenyl, heterocyclyl, or an optionally substituted aryl, arylalkyl, or arylalkenyl.

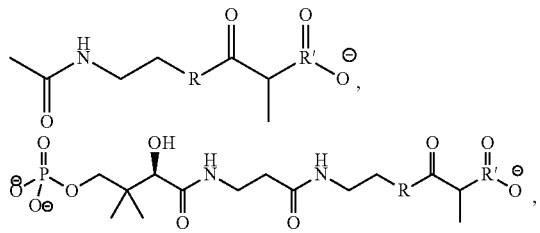

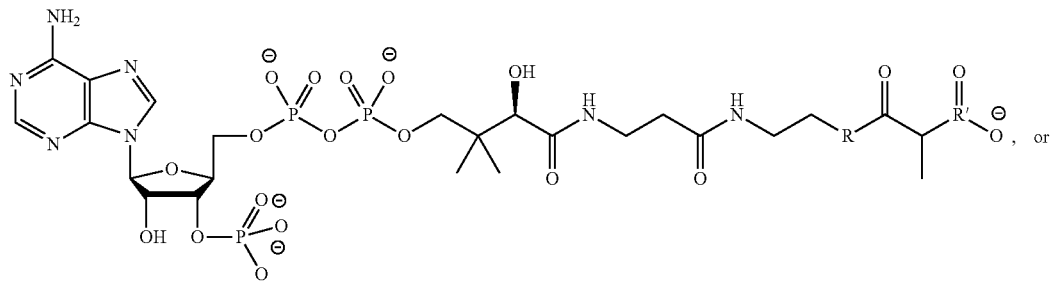

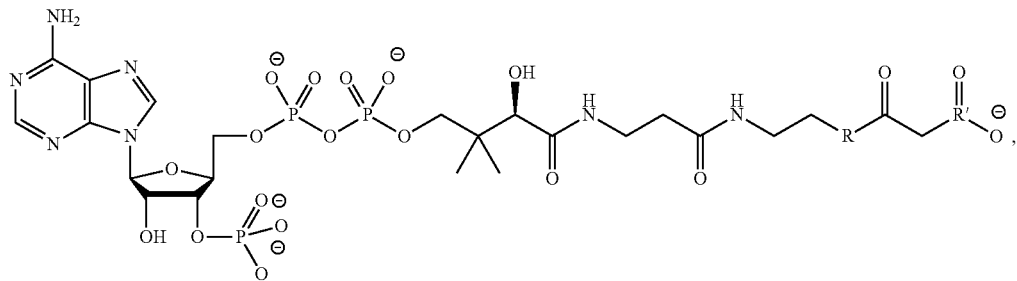

In some illustrative embodiments, the invention is related to a compound of formula (I), wherein X is

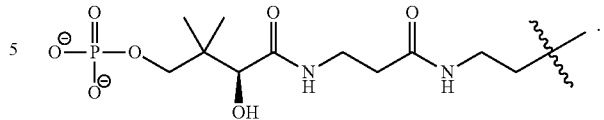

In some illustrative embodiments, the invention is related to a compound of formula (I),
wherein said compound is

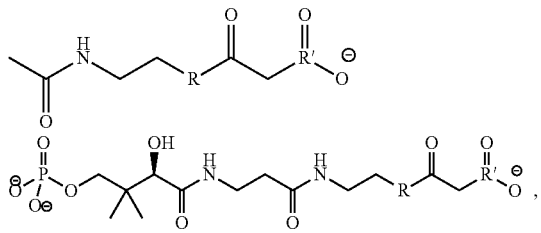

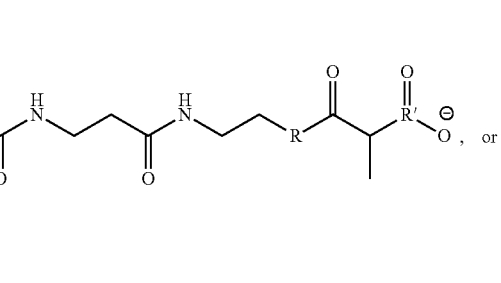

wherein R=S, O, NH; and R'=SO, N$^+$.

In some other illustrative embodiments, the invention is related to a pharmaceutical composition comprising one or more compounds of formula (I), or a pharmaceutically acceptable salt thereof, together with one or more diluents, excipients or carriers.

In some other illustrative embodiments, the invention is related to a pharmaceutical composition comprising one or more compounds of claim 1, or a pharmaceutically acceptable salt thereof, in combination with one or more other compounds of the same of different mode of action, together with one or more diluents, excipients or carriers.

In some other illustrative embodiments, the invention is related to a method for treating a disease mediated by fatty acid synthase malfunction, such as infection diseases, can- In some illustrative embodiments, the invention is related to a compound of formula (I), wherein R$_1$ is hydrogen, a C$_1$-C$_{24}$ alkyl or an optionally substituted C$_6$-C$_{24}$ aryl.

In some illustrative embodiments, the invention is related to a compound of formula (I), wherein R$_1$ is hydrogen.

In some illustrative embodiments, the invention is related to a compound of formula (I), wherein R$_1$ is a C$_1$-C$_{24}$ alkyl.

In some illustrative embodiments, the invention is related to a compound of formula (I), wherein R$_1$ is methyl.

In some illustrative embodiments, the invention is related to a compound of formula (I), wherein X is coenzyme A (CoA).

cers, metabolic diseases, inflammation, and immunological disorders, comprising the step of administering a therapeutically effective amount of one or more compounds of formula (I) as disclosed herein, and one or more carriers, diluents, or excipients, to a patient in need of relief from said disease.

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) in combination with one or more other compounds of the same or different mode of action, and one or more carriers, diluents, or excipients, to a patient in need of relief from said disease.

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein formula (I) is

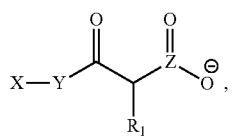

wherein
X is co-enzyme A (CoA),

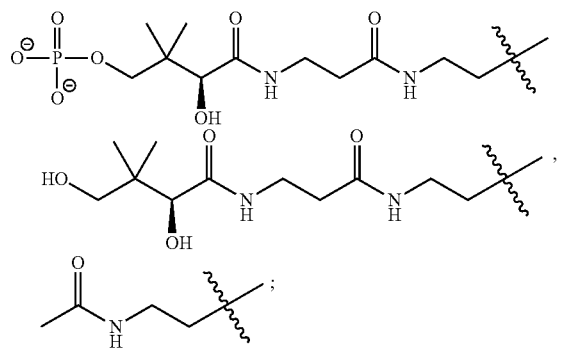

Y is methylene (—CH$_2$—), S, SO, NR, NH, or O;
Z is N$^+$, S or SO; and
R$^1$ is hydrogen, an alkyl, alkenyl, alkynyl, heteroalkyl, heteroalkenyl, heteroalkynyl, cycloalkyl, heterocyloalkyl, cycloalkenyl, heterocycloakenyl, heterocyclyl, or an optionally substituted aryl, arylalkyl, or arylalkenyl.

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein R$_1$ is hydrogen, a C$_1$-C$_{24}$ alkyl or an optionally substituted C$_6$-C$_{24}$ aryl.

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein R$_1$ is hydrogen.

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein R$_1$ is a C$_1$-C$_{24}$ alkyl.

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein R$_1$ is methyl.

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein X is coenzyme A (CoA).

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein X is

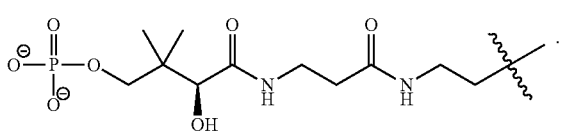 [SMILES: *CCNC(=O)CCNC(=O)[C@@H](O)C(C)(C)COP(=O)([O-])[O-]]

In some other illustrative embodiments, the invention is related to a method for treating a disease mediated by fatty acid synthase malfunction, such as infection diseases, cancers, metabolic diseases, inflammation, and immunological disorders, comprising the step of administering a therapeutically effective amount of one or more compounds of formula (I) or a pharmaceutically acceptable salt thereof, together with one or more carriers, diluents, or excipients, to a patient in need of relief from said disease, wherein said compound is

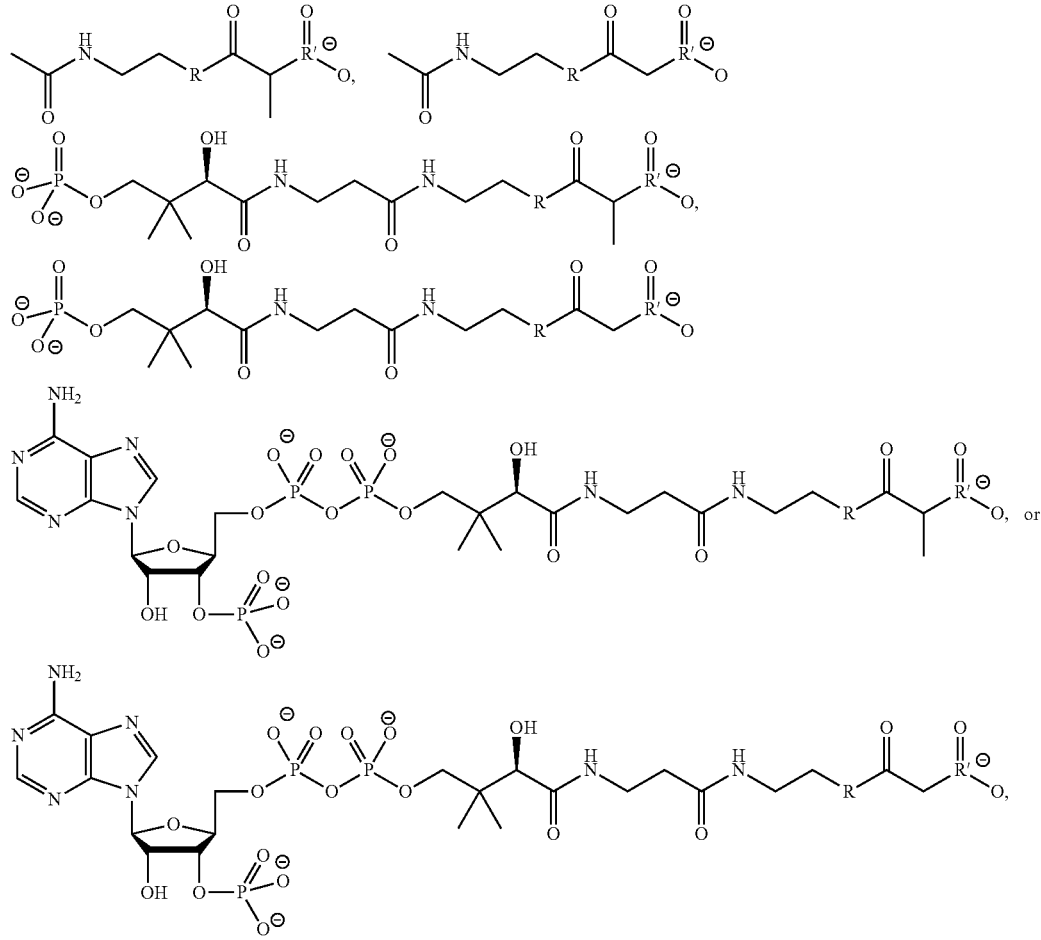

wherein R=S, O, NH; and R'=SO, N⁺.

In addition, it is appreciated herein that the compounds described herein may be used in combination with other compounds that are administered to treat other symptoms, such as compounds administered to relieve pain, nausea, vomiting, and the like.

Hydrolysis and decarboxylation reactions of malonyl-CoA and 2-substituted analogs like methylmalonyl-CoA (1) are spontaneous and essentially irreversible (Kulkarni R A, et al., Cell Chem Biol 2017, 24(2), 231-242). While the uncatalyzed hydrolysis and decarboxylation reactions are slow, enzymes acting on malonyl-CoAs activate the malonyl-thioester leading to an increase in the rate of non-productive side reactions. This reactivity prohibits determination of structures with malonyl-CoAs bound to enzymes such as acyl-CoA carboxylases, transcarboxy transferases, acyltransferases and β-ketoacylsynthases found in fatty acid, polyketide and other specialized metabolite biosynthetic pathways. Structures of these enzymes in complex with malonyl-CoAs or malonyl-thioesters are necessary for understanding the molecular interactions governing catalysis for inhibitor design or enzyme engineering. To overcome problems associated with natural malonyl-thioesters in structure-function studies, we have synthesized methylmalonyl-CoA analogs bearing novel methylmalonyl-thioester isosteres with the carboxylate changed to a sulfonate or nitro. Application of these methylmalonyl-CoA analogs to study Escherichia coli methylmalonyl-CoA decarboxylase (YgfG, MMCD) structure-function relationships provides proof-of-principle for use with other enzymes.

Previously synthesized malonyl-CoA analogs found in crystal structures can bind in non-catalytic orientations. The first malonyl-CoA analog found in a crystal structure is 2-carboxypropyl-CoA (2) a thioether analog of 1, FIG. 1. Alteration of the thioester to a thioether makes the analog stable to hydrolysis and decarboxylation. The thioether 2 is a good mimic for 1 in the structure of Propionibacterium shermanii methylmalonyl-CoA mutase (PDB 7REQ). However, 2 binds in the active site of MMCD inconsistent with any reasonable catalytic mechanism (PDB 1EF9) (Benning, M M, et al., Biochemistry 2000, 39(16), 4630-4639). Recently, a malonyl-S-phosphopantethine analog bearing an oxetane (3) was reported in the active site of a DpsC (PDB 5WGC), a polyketide synthase enzyme using malonyl-S-acyl carrier protein as a substrate (Ellis B D, et al., J. Am. Chem. Soc. 2018, 140(15), 4961-4964). However, the oxetane oxygen was oriented toward solvent, obscuring the role of the thioester ketone in catalysis. Both 2 and 3 are altered at the thioester oxygen, which is necessary for 1) stabilizing the enolate formed upon decarboxylation of malonyl-thioesters and 2) transfer of the malonyl-group to nucleophiles. Alternative malonyl-thioester isosteres that retain the thioester ketone require changing the carboxylate to eliminate decarboxylation, inspiring us to generate methylmalonyl-CoA analogs 4-9, FIG. 1.

Carboxylate isosteres are well known in medicinal chemistry, but there is little literature concerning β-keto carboxylate isosteres, especially for mechanistic enzymology. There are two main types of carboxylate isosteres, cyclic and acyclic (Ballatore C, et al., Chem Med Chem 2013, 8(3), 385-395; Lassalas, P, et al., J. Med. Chem. 2016, 59(7), 3183-3203). Cyclic isoesters such as tetrazoles are too bulky to act as accurate mechanistic probes. The same is true of acyclic isoesters like hydroxamic acids and sulfonamides. Sulfonate and sulfinate isosteres carry a negative charge at physiological pH similar to the carboxylate of 1, but have deviations in geometry due to extra electrons or an oxygen. Phosphonate and phosphinate isosteres carry two negative charges at physiological pH and differ in geometry, making them less suitable than sulfinates/sulfonates. Nitro isosteres of carboxylates are relatively common when attached to a benzene ring. However, alkyl-nitro and especially β-keto nitro groups are relatively uncommon. In solution, β-keto alkyl nitro groups are in equilibrium with the nitronate form, which carries a charge on the oxygen atoms, mimicking a carboxylate.

With the above in mind and an awareness that the thioester may need to be changed to an ester or amide for stabilization against hydrolysis, we synthesized 4-9 as outlined in Schemes 1-3. Our strategy was to produce acetonide protected pantetheine (10), oxypantetheine (11) and aminopantetheine (12), followed by alkylation of all three with 2-bromopropionyl bromide to yield 13-15. This required generation and reduction of acetonide protected pantethine (16), and coupling of ethylenediamine or ethanolamine to acetonide protected pantoththenic acid (17) via ethylchloroformate (ECF). The sulfinate is produced by addition of sodium dithionite to the bromides 13-15 in a water/methanol mixture. The sulfinate products, 18-20, were confirmed by LC/MS. However, upon purification away from the dithionite reactant/reductant, the sulfinates spontaneously oxidize to sulfonates 21-23. To generate the nitro analogs, 13-15 were treated with an excess of sodium nitrite in DMF with phloroglucinol to yield the β-keto nitro intermediates (24-26), which was inspired by previous literature(Kornblum N., et al., J. Am. Chem. Soc. 1957, 79(10), 2507-2509). Finally 21-23 and 27-29 were generated through TFA catalyzed deprotection and converted to the CoAs (4-9) chemoenzymatically. We would like to note that if bromoacetyl bromide is used to generate the corresponding pantetheine-bromoacetate, nitration gives extremely poor yields. Thus, this procedure is not suitable for the production of malonyl-thioester mimics with nitro isoesters. The preparation and characterization of those intermediates and final product compounds are detailed in the experimental section.

To provide proof-of-principle that our analogs are useful for structure-function studies we examined them in complex with MMCD, since details for how the methylmalonyl-CoA carboxylate binds and how the enolate was protonated were still unclear from studies with 2. Co-crystallization of an almost native MMCD (single S2A mutation) with 4-9 yielded structures with active site density for the analogs that provides insight into the positioning of the methylmalonyl-moiety in the active site prior to decarboxylation, FIGS. 2A-2C. Our structures were determined at resolutions between 1.69 to 1.80 Å with reasonable data collection and refinement statistics, see Table S1 for details. Each unit cell contains a hexamer with each monomer having a substrate analog bound, allowing for six independent determinations of binding orientation. The monomer designated chain A is in the same unit cell location in all six structures, and contained the clearest methylmalonyl-CoA analog electron density (except for 8 where chain E was clearest). An interesting finding is that the nitro analogs 7-9 mostly bound in the nitronate form, based on the methyl group being planar to both the nitro and C1 ketone, FIGS. 2A-2C. The amide-nitro analog 9 is found with a nitro oxygen hydrogen bonded back to the amide FIGS. 2B and 2C. The residual density for 7 and 8 in many active sites can be explained by either multiple orientations in the active sites, or degradation of the isostere via hydrolysis, reduction to an oxime or the Nef reaction. The reduction and hydrolysis reactions are supported by a pyruvate oxime found in crystal contacts of MMCD structures with 7 or 8. Our crystals were grown in the presence of 10 μM $NiSO_4$, which may have catalyzed reduction to the oxime, which is curious since exogenous reductants were not added. Nevertheless the results here suggest 4-6 and 9 are stable enough to be used in other enzyme systems where hydrolysis is a concern.

Figure 2A:
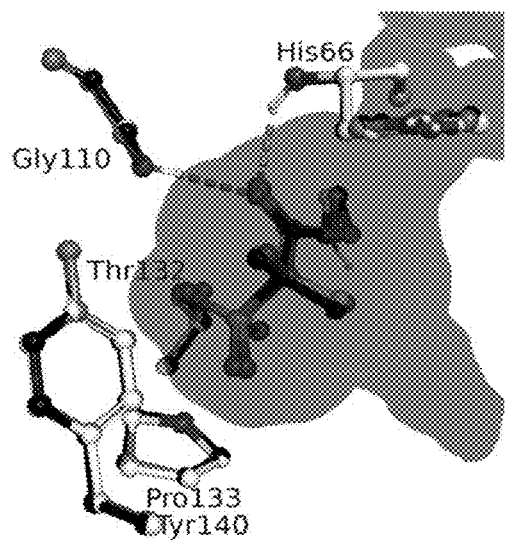
FIG. 2A shows isostere binding in methylmalonyl-Co-A decarboxylase (MMCD) active site of superimposition of MMCD chain A with 4, 5 and 6 bound, colored black, gray and white, respectively. Both C-1 stereoisomers were modeled in the active site for 4-6. The surface of the cavity is shown surrounding the analogs for structure with 4 bound, notice that the imidazole of His66 contacts the solvent surface.
Figure 2B:
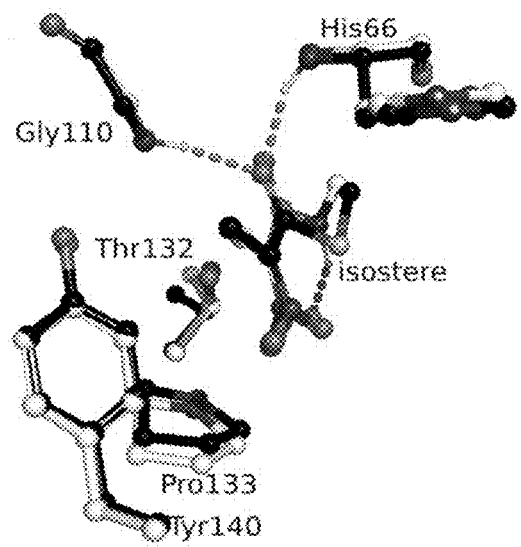
FIG. 2B shows comparison of MMCD chain A with 7 and 9 bound, colored black and white, respectively. Note that the amide and nitro of 9 are hydrogen bonded as shown by red dashes.
Figure 2C:
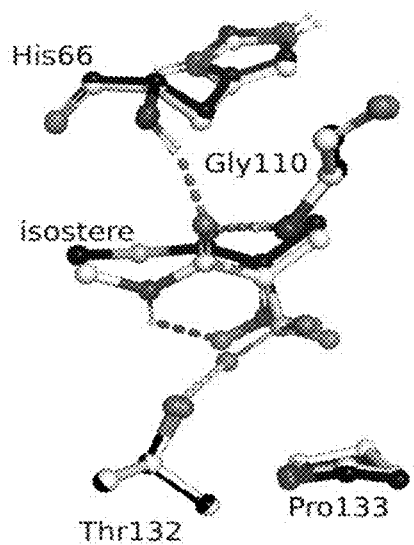
FIG. 2C shows comparison of structures with 4 and 7 bound, the carboxylate isosteres are in similar positions, suggesting the carboxylate interacts with Pro133. The yellow dashed indicate a potential hydrogen bond.

The thioester carbonyl retained in our isosteres interacts with the previously identified oxyanion hole created by amides of His66 and Gly110, as expected, FIGS. 2A-2C. In the study using 2, it was predicted that the carboxylate would hydrogen bond with the hydroxyl of Tyr140 (Benning, M M, et al., Biochemistry 2000, 39(16), 4630-4639). However, the closest contact for the nitro and sulfonate moieties of our analogs is with Pro133. The rest of the binding pocket is mostly hydrophobic, generated by residues Ile68, Leu71, Leu79, Leu85, Gly109, Met131, Leu136, Val138 and Tyr140. An exception is Thr132 which interacts with an oxygen on the sulfonyl-isosteres. The observation that both nitro and sulfonate groups bind near Pro133 in the hydrophobic pocket strongly suggests the natural carboxylate binds in a similar location, FIG. 2C.

It is likely Thr132 temporarily interacts with the methylmalonyl carboxylate on path to the hydrophobic pocket and interaction with Pro133. Binding of the thioester carbonyl in the oxyanion hole formed by Bly110 and His66 backbone amides stabilizes the enolate resulting from decarboxylation, resulting in neutral $CO_2$ bound in the hydrophobic pocket. To prevent reversion (addition of $CO_2$ back to the enolate. Kluger R. Acc Chem. Res 2015, 48(11), 2843-2849), a protonated His66 side chain rotates into the active site to protonate the enolate yielding the propionyl-CoA product. The role of His66 as a proton donor is apparent when comparing binding of the carboxylate of thioether 2, and C, O and Ca atoms of our analogs. In the majority of our structures, the His66 imidazole is protonated and has an interaction with the Asp83 carboxylate and a weak hydrogen bond to the Asp67 peptide ketone. In a few cases, the His66 sidechain is neutral and interacts with the Asp83 carboxylate and Asp67 amide hydrogen. These two different binding orientations of His66 may alter substrate affinity since the His66 backbone carbonyl and adjacent Ile68 amide contact the CoA adenine. Evidence for the role of His66 in enolate protonation comes from activity assays.

Kinetic characterization of MMCD was originally performed using a coupled assay with transcarboxylase generating (2S)-methylmalonyl-CoA at pH 7.2 and 37° C. that was not optimized, leading to a reported $K_m$ of 13.6 μM and $k_{cat}$ of 1.6 s$^{-1}$, $k_{cat}/K_m$ 0.12 μM$^{-1}$i$^{-1}$ (Haller, T, et al., Biochemistry 2000, 39(16), 4622-4629). Here we used direct detection of product formation from racemic 1 with a HPLC assay at 25° C. An underestimate for $k_{cat}/K_m$ in our system is 0.17 µM$^{-1}$s$^{-1}$. A pH rate profile reveals maximum decarboxylation activity is below pH 6.0 and decreases with increasing pH giving a p$K_a$ of 7.4. The p$K_a$ is in line with a protonated His66 acting as a catalytic acid, lending support for the model of catalysis outlined above. We noticed that 1 was hydrolyzed with a significant rate with a maximum at pH 6.8. The hydrolysis could be described by two titratable groups with p$K_a$s of 5.3 and 8.5. This hydrolysis side reaction is expected for an enzyme activating the thioester ketone. CoA is generated from methylmalonyl-CoA rather than from propionyl-CoA, as revealed by no further increase in CoA upon depletion of methylmalonyl-CoA at later time points in the enzyme assays.

Initially we attempted to use isothermal titration calorimetry to determine the binding affinity of our analogs to MMCD. We were not able to determine $K_d$s due to artifacts suggesting MMCD could not be saturated. Examination of electron density surrounding the active site revealed a second coenzyme A binding site in approximately half of the monomers, typically chains C/E/F. Occupancy of CoA in this allostereic site alters the conformation of Trp108, which directly interacts with methylmalonyl-CoA in the catalytic site. Because of this secondary site causes problems with biophysical characterization of binding affinity, we used the $k_{cat}/K_m$ approximation at low substrate concentrations for the determination of inhibition constants for our analogs. These assays gave $K_i$s of 7.5±1.1 µM for 4, 3.8±1.6 µM for 5, 7.1±1.7 µM for 6, 10.8±2.3 µM for 7, 20.6±2.7 µM for 8 and 19.8±1.4 µM for 9. The sulfonate isosteres bind tighter than the nitro isosteres in general. Our results have been published and incorporated herein by reference in its entirety (Stunkard, L M, et al., *J. Am. Chem. Soc.* 2019, 141, 5121-5124).

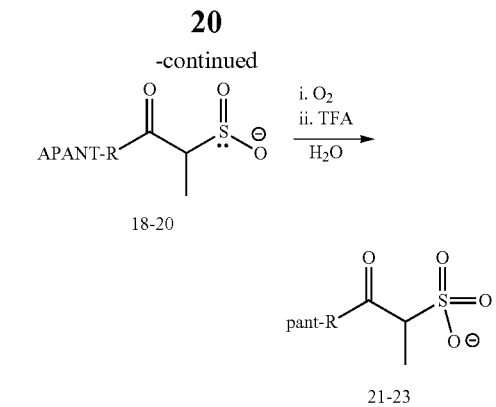

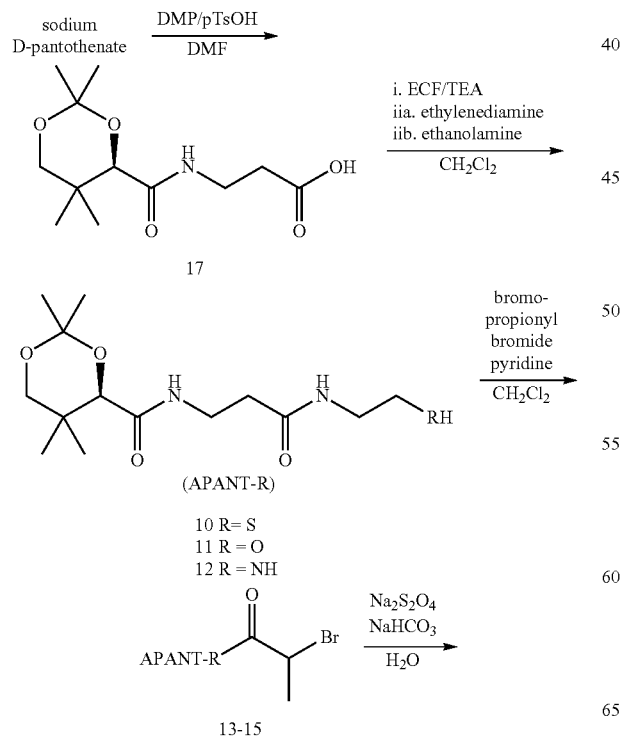

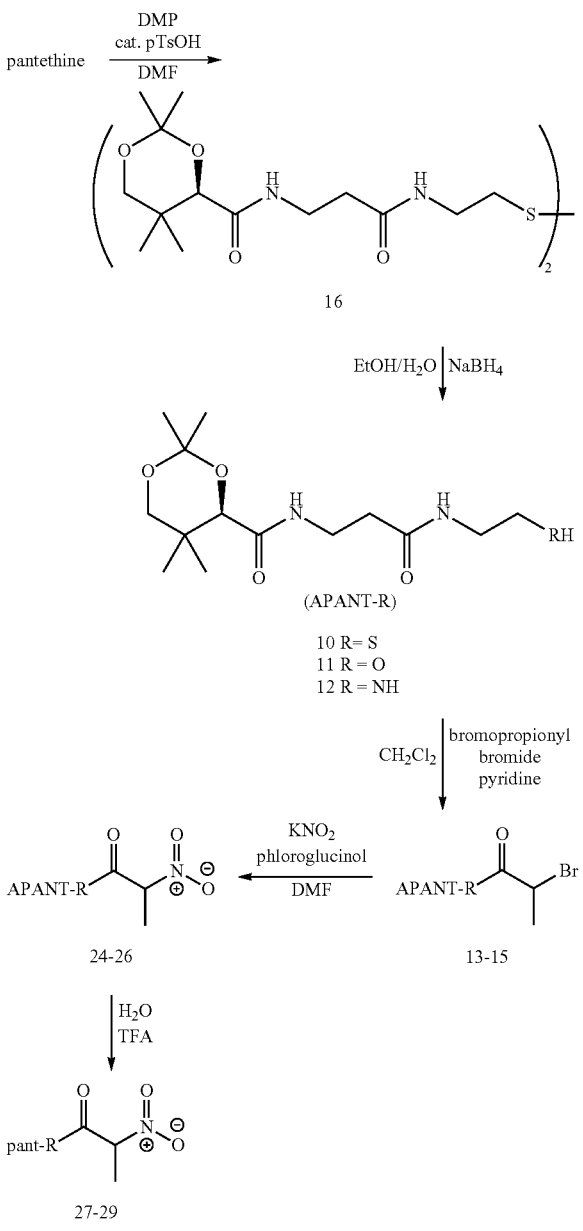

Scheme 3. Synthesis final product compounds 4-9

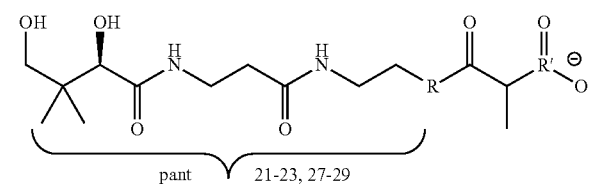

R = S, O, NH
R' = N+, SO

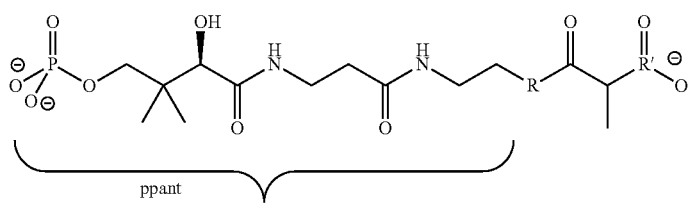

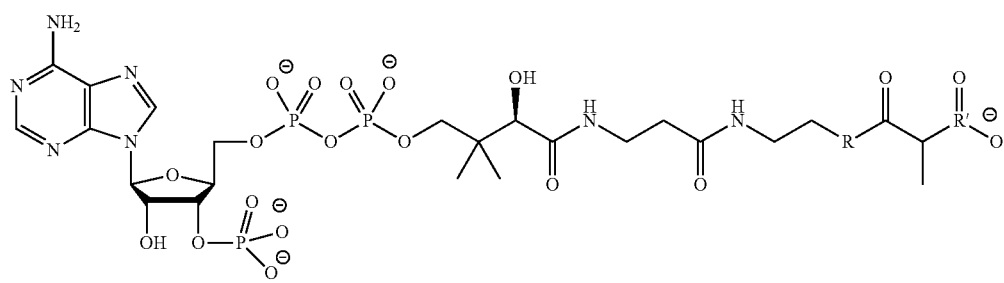

4-9

Additionally, we synthesized stable malonyl-CoA analogs using a diversity oriented synthetic strategy as in Scheme 4, similar to our previous synthesis of stable methylmalonyl-CoA analogs, which was inspired by previous syntheses of acyl-CoAs and analogs. Acetonide protected pantetheine (31), oxy(dethia)pantetheine (32) and amino(dethia)pantetheine (33) were generated as previously published. The acetonide pantetheine analogs 31-33, N-acetylcysteamine (34, SNAC), N-acetylethanolamine (35) and N-acetylethylenediamine (36) were treated with bromoacetyl bromide with pyridine as a base to give bromoacetyl-pantetheine acetonides (37-39), and bromoacetyl-SNACs (40-42). The bromoacetyl pantethine analogs 37-42 were treated with sodium dithionite to yield 2-sulfinateacetyl-pantethine analogs (43-48). Upon sitting overnight the sulfinates oxidize to the sulfonates (49-54). Finally the acetonides are deprotected in TFA/water and the sulfonic acids are purified by reverse phase preparative chromatography.

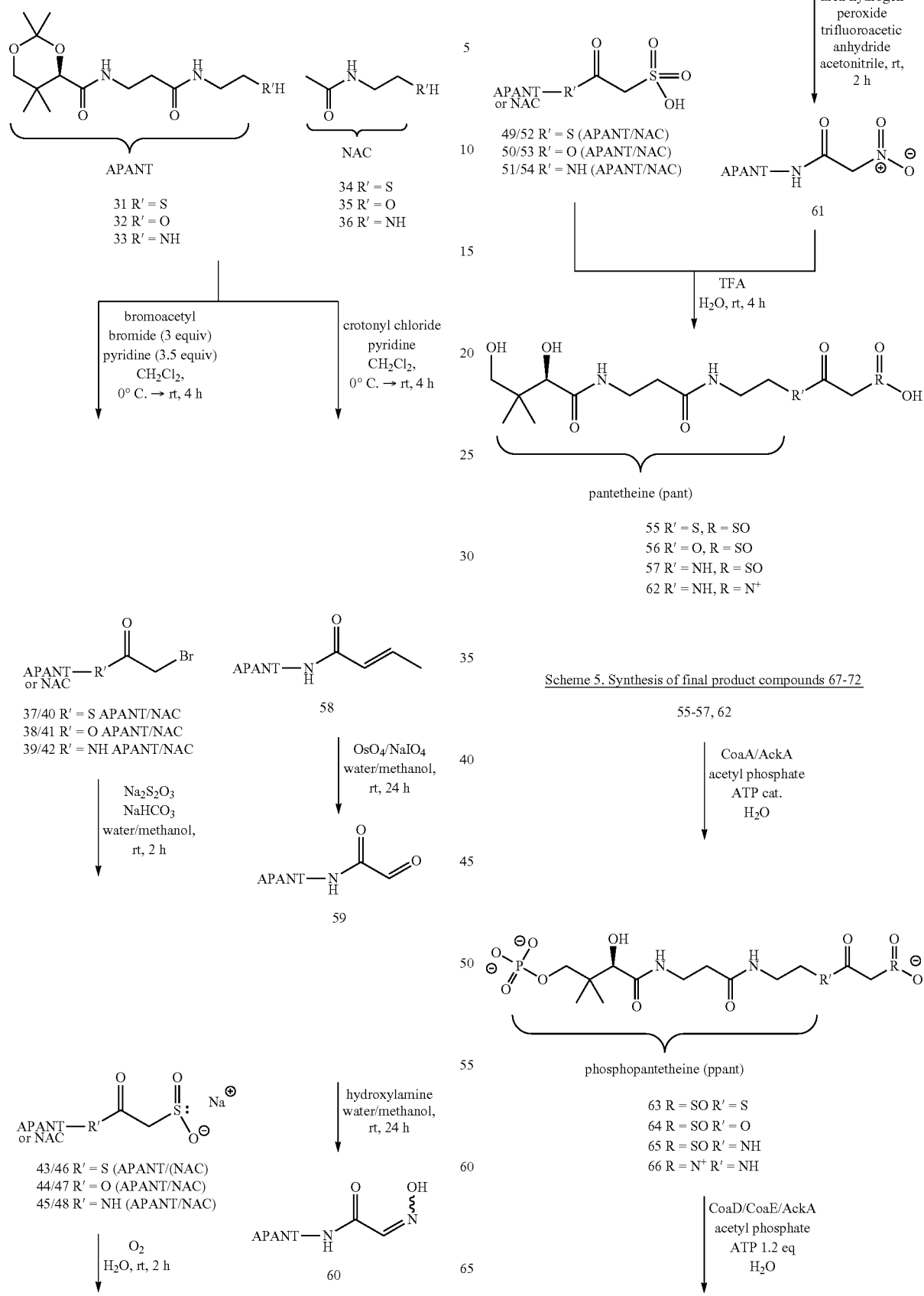

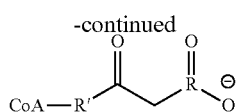

67 R = SO R' = S
68 R = SO R' = O
69 R = SO R' = NH
70 R = N⁺ R' = NH

Sfp
ACP
H₂O

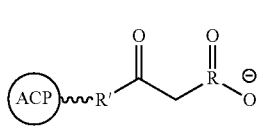

71 R = SO R' = NH
72 R = N⁺ R' = NH

Our pervious synthetic route to nitro-bearing methylmalonyl-CoA analogs, via acetonide protected 2-bromopropionyl-pantetheine intermediates was not applicable to generating the respective malonyl-CoA analogs. Reaction of the 2-bromopropionyl group with potassium nitrite in DMF with the presence of phloroglucinol lead to reasonable yields of the nitro product. The same reaction with bromoacetyl-pantetheine results in very poor yields. Therefore we had to take a new approach. Alternatively, 33 was treated with crotonyl chloride to give crotonyl-amido(dethia)pantethine acetonide (58), which was treated with osmium tetroxide and sodium periodate in water to give glyoxylate-amido(dethia)pantetheine acetonide (59). The glyoxylate was converted to an oxime (60) upon treatment with hydroxylamine and subsequently converted to the nitro (61) with trifluoroacetic peroxide via urea-hydrogen peroxide complex with trifluoroacetic anhydride. The acetonides 37-40 and were deprotected with TFA in water and chemoenzymatically converted to the CoA or phosphopantetheine analogs, using the improved method developed in the accompanying paper, Scheme 5. Compounds 2-sulfonate-acetyl-CoAs can also be prepared from bromoacetyl- or chloroacetyl-CoA, which have been previously synthesized. This creates an opportunity to generate the sulfinates in situ, due to their essentially complete conversion.

Materials and Methods

Chemicals and solvents: All chemicals were purchased from Acros, Aldrich, Alfa Aesar, Fluka, Oakwood or TCI America and used without further purification. For reactions, technical grade solvents were used without further purification and dried over molecular sieves (size type here) when applicable. HPLC grade solvents were used for flash chromatography, analytical and preparative HPLC. Deuterated solvents were purchased from Acros or Sigma-Aldrich.

Reactions: All organic synthesis reactions were performed under normal atmosphere at room temperature unless otherwise noted. The reactions and purifications were not optimized. Reactions were magnetically stirred with Teflon coated stirbars. Flash chromatography was performed on a CombiFlash Rf200 (Teledyne ISCO) with 24 or 40 gram silica Flash Columns. Preparative HPLC chromatography was performed on an Agilent 1100 preparative HPLC with diode array UV/Vis detection over a Luna 5μ C18(2) 100 Å 250×21.2 mm column (Phenomenex). The reported yields are post purification and spectroscopically pure unless previously reported or otherwise indicated.

Analysis: Reactions and products were characterized by HPLC-MS on an Agilent 1100 HPLC with diode array UV/Vis detection over a Luna 5 μm C18(2) 100 Å 50×2 mm (Phenomenex) or Luna 5 μm C18(2) 100 Å 250×4.6 mm (Phenomenex) with low resolution mass spectrometry (LRMS) analysis in positive and negative modes by an Agilent 1100 G1946D quadrupole with electrospray ionization (ESI). NMR spectra were collected on a Bruker AV500HD equipped with a 5 mm BBFO Z-gradient cryoprobe in the solvents indicated. $^1$H and $^{13}$C NMR spectra are referenced using the signals of the residual undeuterated solvent (CDCl₃ $^1$H-7.27 ppm and $^{13}$C-77.14 ppm, DMSO $^1$H-2.48 ppm and $^{13}$C-39.5 ppm and D₂O $^1$H-4.68 ppm) and where applicable tetramethylsilane 0-ppm. All spectra were collected at 298 K. Chemical shifts are reported in parts per million (ppm) and multiplicities are abbreviated as follows: s (singlet), d (doublet), t (triplet), q (quartet), m (multiplet), and br (broad). Coupling constants (J) are reported in Hertz (Hz).

II. List of Abbreviations

| ACN | acetonitrile; | ATP | adenosine triphosphate |
|---|---|---|---|
| CF | chloroform; | DCM | dichloromethane |
| DMF | dimethylformamide; | DMP | 2,2-dimethoxypropane |
| ECF | ethylchloroformate; | EtOAc | ethyl acetate |
| EtOH | ethanol; | pTsOH | p-toluenesulfonic acid |
| TEA | triethanolamine; | TFA | trifluoroacetic acid |

III. Experimental Procedures and Characterization Data

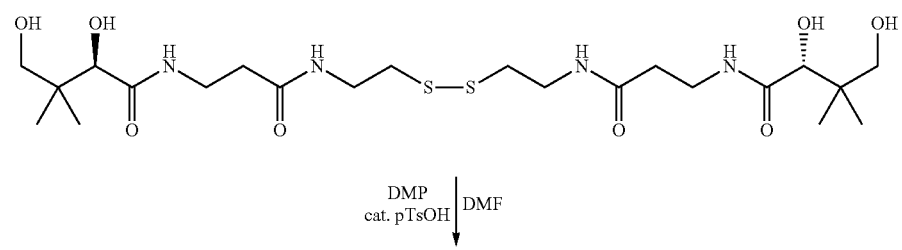

DMP
cat. pTsOH | DMF

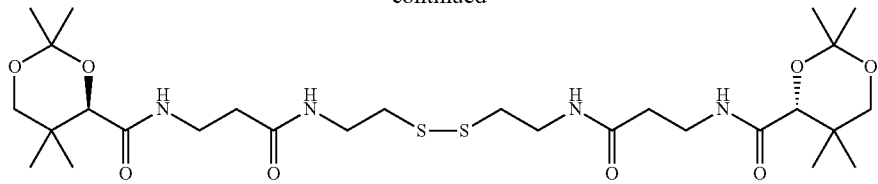

D-pantethine acetonide (16)

(Ma, M, et al., *Proc. Natl. Acad. Sci. USA* 2015, 112, 10359-10364):

To a solution of DMF containing 380 mg (2.00 mmol) of pTsOH.H$_2$O and 10 grams (18.03 mmol) of D-pantethine syrup, 360 mL (2.9 mol) of DMP was slowly added.[1] The reaction was allowed to stir for 12 hours at room temperature and was quenched with solid sodium bicarbonate. The solvent was removed leaving a white precipitant which was suspended in DCM and filtered. The solvent from the flow through was removed yielding 16 as an oil that slowly crystallized (10 g, 15.75 mmol 87.4%).

$^1$H NMR (500 MHz, CDCl$_3$) δ 7.67 (br, 2H, NH), 7.12 (br, 2H, NH), 4.00 (s, 2H), 3.62 (d, J=11.6 Hz, 2H), 3.57-3.38 (m, 8H), 3.20 (d, J=11.7 Hz, 2H), 2.76 (t, J=6.9 Hz, 4H), 2.43 (t, J=6.5 Hz, 4H), 1.37 (s, 6H), 1.39 (s, 6H), 0.96 (s, 6H), 0.91 (s, 6H). $^{13}$C NMR (126 MHz, CDCl$_3$) δ 171.38, 169.57, 98.70, 76.83, 71.00, 38.27, 37.42, 35.27, 34.72, 32.63, 29.20, 21.90, 18.70, 18.48. LRMS (ESI) m/z calculated for C28H50N4O8S2H ([M+H]$^+$) 635.31, found 635.3.

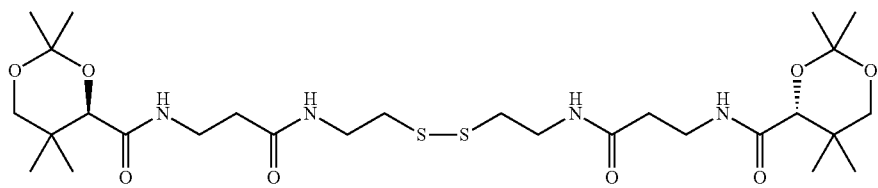

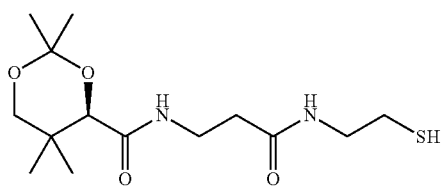

D-pantetheine acetonide (10)

(Crawford, J M, et al., *Proc. Natl. Acad. Sci. USA* 2006, 103, 16728-16733):

To a solution of 16 (10 grams, 15.75 mmol) in ethanol, sodium borohydride (15.7 grams, 415 mmol) was added. The reaction was allowed to stir for 6 hours at room temperature. The reaction was carefully quenched with acetic acid to pH 5.0. The solvent was removed, re-suspended in DCM and filtered. The flow through solvent was removed and the remaining residue was subjected to flash chromatography (0→100% gradient of hexanes→EtOAc) to afford 10 (transparent oil, 8.5 g, 26.69 mmol, 84.7%).

$^1$H NMR (500 MHz, CDCl$_3$): δ 7.05 (br, 1H, NH), 6.42 br, 1H, NH), 4.08 (s, 1H), 3.67 (d, J=11.8 Hz, 1H), 3.62-3.48 (m, 2H), 3.48-3.33 (m, 2H), 3.27 (d, J=11.7 Hz, 1H), 2.70-2.59 (m, 2H), 2.51-2.44 (m, J=6.8, 5.7, 3.8 Hz, 2H), 1.45 (s, 3H), 1.41 (s, 3H), 1.02 (s, 3H), 0.96 (s, 3H). $^{13}$C NMR (126 MHz, CDCl$_3$) δ 171.24, 170.50, 99.14, 76.78, 71.39, 42.47, 36.12, 34.99, 32.99, 29.46, 24.51, 22.11, 18.92, 18.70. LRMS (ESI) m/z calculated for C14H26N2O4SH ([M+H]$^+$) 319.16 and ([M–H]$^-$) 317.16, found 319.2, 317.1, respectively.

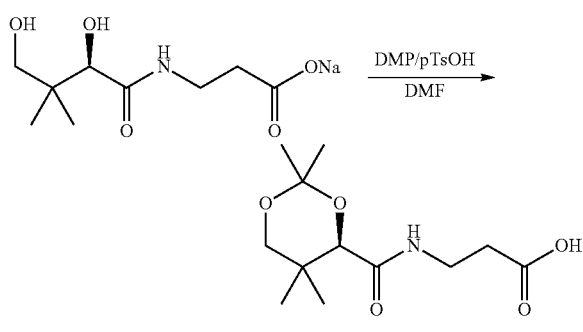

17

O,O'-isopropylidene-D-pantothenic Acid (17)

To a solution of DMF containing 3.94 g (20.7 mmol) of pTsOH.H$_2$O and 5 g (20.7 mmol) of sodium D-pantothenate, 200 mL (1.6 mol) of DMP was slowly added.[4] The reaction was allowed to stir for 12 hours at room temperature. The solvent was removed leaving a white precipitant that was suspended in DCM and filtered. The solvent was removed yielding 17 (crystalline oil, 5.4 g, 20.83 mmol 100%). Spectroscopic data are consistent with previously reported data.

LRMS (ESI) m/z calculated for C12H21NO5 ([M+H]$^-$) 258.14, found 258.1.

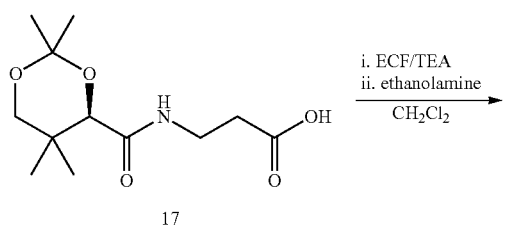

17

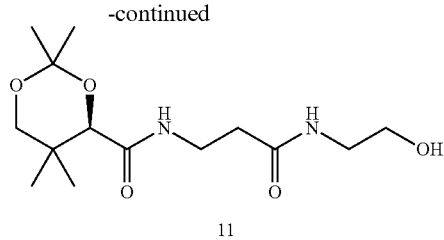

11 oxa(dethia)pantetheine acetonide (11)

To a solution of DCM containing 17 (5.9 g, 22.75 mmol) and TEA (4 mL, 28.68 mmol) at 4° C., ECF (2.5 mL, 26.27 mmol) was added slowly (Tosin, M, et al., *Chembiochem* 2009, 10, 1714-1723). The reaction was allowed to stir for 15 minutes at 4° C. Then ethanolamine (2 mL, 33.14 mmol) was added to the reaction dropwise. The reaction was allowed to stir for 12 hours. The solution was transferred to a separatory funnel. The mixture was diluted with CF and then washed with brine. The organic layer was collected. The brine mixture was back extracted with CF. The organic layers were pooled and dried with anhydrous sodium sulfate. The solvent was removed yielding 11 (off white powder, 5.72 g, 18.9 mmol 83.1%).

$^1$H NMR (500 MHz, CDCl$_3$) δ 7.04 (br, 1H, NH), 6.54 (br, 1H, NH), 4.07 (s, 1H), 3.75-3.63 (m, 3H), 3.61-3.51 (m, 2H), 3.48-3.36 (m, 2H), 3.28 (d, J=11.7 Hz, 1H), 2.48 (t, J=6.3 Hz, 2H), 1.46 (s, 3H), 1.42 (s, 3H), 1.03 (s, 3H), 0.97 (s, 3H). $^{13}$C NMR (126 MHz, CDCl$_3$) δ 171.94, 170.61, 99.17, 76.77, 71.39, 62.20, 42.53, 36.38, 35.00, 32.98, 29.45, 22.12, 18.87, 18.68. LRMS (ESI) m/z calculated for C14H26N2O5H ([M+H]$^+$) 303.19, found 303.1.

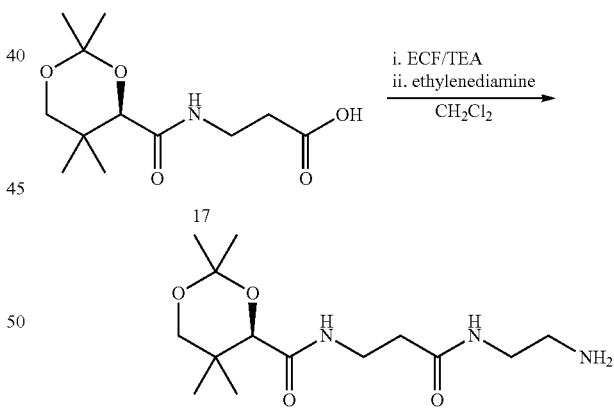

12 amino(dethia)pantetheine acetonide (12)

To a solution of DCM containing 17 (5 g, 19.28 mmol) and TEA (6 mL, 28.68 mmol) at 4° C., ECF (4 mL, 28.68 mmol) was added slowly (Li H, et al., *Biochemistry* 2011, 50, 9532-9544). The reaction was allowed to stir for 15 minutes at 4° C. Then the reaction was slowly added to a solution of DCM containing ethylenediamine (20 mL, 300 mmol). The reaction was allowed to stir for 12 hours. The solvent was removed and the remaining oil was subjected to flash chromatography (0→100% gradient of DCM→MeOH) affording 12 (oil, 5.2 g, 17.25 mmol 89.5%).

$^1$H NMR (500 MHz, CDCl$_3$) δ 7.06 (br, 1H, NH), 6.50 (br, 1H, NH), 4.06 (s, 1H), 3.66 (d, J=11.7 Hz, 1H), 3.63-3.43 (m, 2H), 3.30-3.22 (m, 3H), 2.80 (t, J=12.7, 7.7 Hz, 2H), 2.44 (t, J=6.3 Hz, 2H), 1.45 (s, 3H), 1.40 (s, 3H), 1.02 (s, 3H), 0.95 (s, 3H). Spectroscopic data are consistent with previously reported data.[5] $^{13}$C NMR (126 MHz, CDCl$_3$) δ 171.29, 170.22, 99.09, 76.79, 71.42, 42.07, 41.34, 36.17, 35.01, 32.96, 29.47, 22.13, 18.88, 18.69. LRMS (ESI) m/z calculated for C14H27N3O4H ([M+H]$^+$) 302.20, found 302.2.

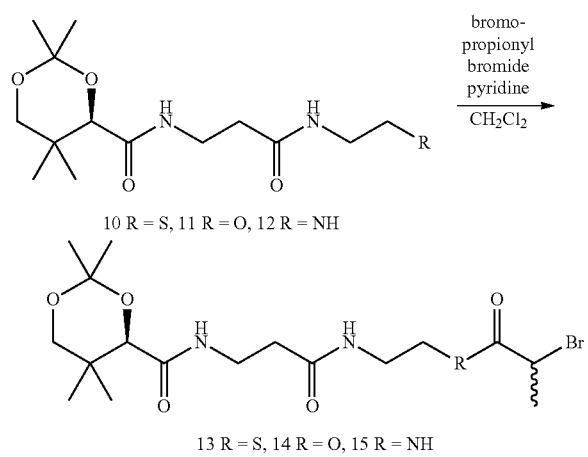

Preparation of 13-15 Via 10-12

General Procedure

A solution of DCM containing 10-12 pyridine was added slowly to a solution of DCM containing bromopropionyl bromide at 4° C. The reaction was allowed to stir for 12 hours while warming to room temperature. The solution was transferred to a separatory funnel. The solution was washed with brine, copper sulfate, and sodium thiosulfate, repeatedly. The solvent was removed and the remaining red/orange oil was subjected to flash chromatography (0→100% gradient of DCM→acetone or MeOH) affording 13-15.

2-bromopropionyl-S-pantetheine acetonide (13)

10 (9.0 g, 28.26 mmol) was reacted with pyridine (19 mL, 235.8 mmol) and bromopropionyl bromide (9.5 mL, 90.7 mmol) according to the general procedure above affording 13 (oil, 1.5 g, 3.31 mmol 11.7%).

$^1$H NMR (500 MHz, CDCl$_3$) δ 7.34 (br, 1H, NH), 7.14 (br, 1H, NH), 4.55 (q, J=6.9 Hz, 1H), 4.08 (s, 1H), 3.69 (d, J=11.7 Hz, 1H), 3.64-3.52 (m, 2H), 3.52-3.38 (m, 2H), 3.27 (d, J=11.7 Hz, 1H), 3.08 (t, 2H), 2.49 (t, J=15.4, 6.4 Hz, 2H), 1.84 (d, J=6.9 Hz, 3H), 1.46 (s, 3H), 1.43 (s, 3H), 1.02 (s, 3H), 0.97 (s, 3H). $^{13}$C NMR (126 MHz, CDCl3) δ 196.20, 171.36, 169.90, 98.89, 76.97, 71.17, 47.81, 38.70, 35.45, 34.81, 32.79, 29.36, 29.10, 22.04, 21.88, 18.85, 18.63. LRMS (ESI) m/z calculated for C17H29BrN2O5SH ([M+H]$^+$) 453.10 and 455.10, found 453.1 and 455.1.

2-bromopropionyl-oxa(dethia)pantetheine acetonide(14)

11 (2.5 grams, 8.27 mmol) was reacted with pyridine (2 mL, 24.83 mmol) and bromopropionyl bromide (1.5 mL, 14 mmol) according to the general procedure above affording 14 (oil, 830 mg, 1.90 mmol 22.9%).

$^1$H NMR (500 MHz, CDCl$_3$) δ 7.32 (br, 1H, NH), 7.20 (br, 1H, NH), 4.43 (q, J=6.8 Hz, 1H), 4.25 (t, J=6.2, 5.7 Hz, 6H), 4.07 (s, 1H), 3.69 (d, J=11.7 Hz, 1H), 3.60-3.47 (m, 4H), 3.27 (d, J=11.7 Hz, 1H), 2.48 (t, J=6.5 Hz, 2H), 1.82 (d, J=7.0 Hz, 3H), 1.46 (s, 3H), 1.43 (s, 3H), 1.02 (s, 3H), 0.97 (s, 3H). $^{13}$C NMR (126 MHz, CDCl$_3$) δ 171.46, 169.99, 169.94, 98.86, 76.90, 71.08, 64.13, 39.91, 37.98, 35.47, 34.80, 32.72, 29.27, 21.97, 21.39, 18.75, 18.57. LRMS (ESI) m/z calculated for C17H29BrN2O6H ([M+H]$^+$) 437.12 and 439.12, found 437.1 and 439.1.

2-bromopropionyl-amino(dethia)pantetheine acetonide (15)

12 (5 g, 16.59 mmol) was reacted with pyridine (5.5 mL, 68.3 mmol) and bromopropionyl bromide (3.6 mL, 34.4 mmol) according to the general procedure above affording 15 (oil, 510 mg, 1.17 mmol 7.1%).

$^1$H NMR (500 MHz, CDCl$_3$) δ 7.53 (br, 1H, NH), 7.32 (br, 1H, NH), 7.08 (br, 1H, NH), 4.34 (q, J=6.9, 4.0 Hz, 1H), 4.00 (s, 1H), 3.60 (d, J=11.7 Hz, 1H), 3.52-3.38 (m, 2H), 3.33-3.24 (m, 6H), 3.19 (d, J=11.8 Hz, 2H), 2.39 (t, J=6.4, 3.3 Hz, 2H), 1.74 (d, J=6.9 Hz, 2H), 1.38 (s, 3H), 1.35 (s, 3H), 0.93 (s, 3H), 0.88 (s, 3H). $^{13}$C NMR (126 MHz, CDCl$_3$) δ 172.34, 170.66, 170.35, 99.08, 76.89, 71.27, 60.87, 43.95, 40.14, 35.87, 35.17, 32.89, 29.39, 22.44, 22.07, 18.87, 18.67. LRMS (ESI) m/z calculated for C17H30BrN3O5H ([M+H]$^+$) 436.14 and 438.14, found 436.1 and 438.1.

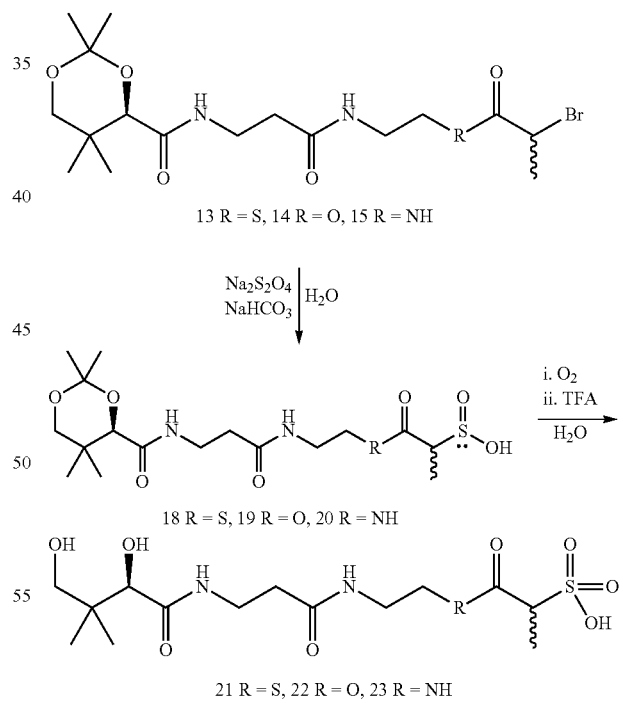

General Procedure for Preparation of 21-23 Via 18-20 Via 13-15

A solution of water containing equimolar sodium dithionite and sodium bicarbonate is allowed to stir for 5 minutes, followed by an addition of a solution of water containing 2-bromopropionyl pantetheine acetonide (13-15). The reaction was allowed to stir at room temperature. After stirring for 30 minutes, HPLC-MS analysis indicated complete conversion of bromides (13-15) to sulfinates (18-20). After stirring for 18 hours, sulfinates (18-20) oxidize to sulfonates (21-23) as indicated by HPLC-MS analysis. The acetonides were deprotected with 15% TFA in water. The resulting solution was subjected to preparative HPLC with a 0→40% gradient of 0.1% TFA in water→methanol over 30 minutes. Solvent was removed affording 18-20.

2-sulfiniatepropionyl-S-pantetheine acetonide (18)

13 (600 mg, 1.32 mmol) was reacted with sodium dithionite (1.22 g, 7.00 mmol) and sodium bicarbonate (588 mg, 7.00 mmol) according to the general procedure above affording 18 (off white powder which was used directly in the next reaction). MS (ESI) m/z calculated for C17H30N2O7S2 ([M−H]$^-$) 437.15, found 437.1.

2-sulfonatepropionyl-S-pantetheine (21)

The deprotection of 18 yielded 21 (off white powder, 50 mg, 0.12 mmol 9.1%, 13→21).

$^1$H NMR (500 MHz, D$_2$O) δ 4.35 (s, 1H), 4.08 (m, 1H), 3.97 (d, J=2.4 Hz, 1H), 3.49-3.43 (m, 3H), 3.25 (t, J=6.7 Hz, 3H), 2.67 (t, J=6.7 Hz, 2H), 2.51-2.39 (m, 3H), 1.15 (s, 3H), 0.87 (s, 3H), 0.84 (s, 3H). $^{13}$C NMR (126 MHz, D$_2$O) δ 180.08, 174.94, 174.00, 77.12, 75.93, 75.61, 40.72, 35.93, 35.48, 35.34, 32.05, 21.48, 20.62, 18.24. MS (ESI) m/z calculated for C14H26N2O8S2 ([M−H]$^-$) 413.11, found 413.0.

2-sulfinatepropionyl-oxa(dethia)pantetheine acetonide (19)

14 (800 mg, 1.83 mmol) was reacted with sodium dithionite (1.92 g, 11.00 mmol) and sodium bicarbonate (924 mg, 11.00 mmol) according to the general procedure above affording 19 (off white powder which was used directly in the next reaction). MS (ESI) m/z calculated for C17H30N2O8S ([M−H]$^-$) 421.17, found 421.1.

2-sulfonatepropionyl-oxa(dethia)pantetheine (22)

The deprotection of 19 yielded 22 (off white powder, 140 mg, 0.35 mmol 19.1%, 14→22).

$^1$H NMR (500 MHz, D$_2$O) 4.24-4.10 (m, 2H), 3.87 (s, 1H), 3.46-3.31 (m, 5H), 3.27 (d, J=11.2 Hz, 1H), 2.39 (t, J=6.5 Hz, 2H), 1.40 (d, 3H), 0.80 (s, 3H), 0.76 (s, 3H). $^{13}$C NMR (126 MHz, D$_2$O) δ 175.01, 174.08, 170.33, 75.76, 68.37, 64.28, 60.50, 38.53, 38.10, 35.35, 35.17, 20.44, 19.03, 12.72. MS (ESI) m/z calculated for C14H26N2O9S ([M−H]$^-$) 397.17, found 397.0.

2-sulfinatepropionyl-amino(dethia)pantetheine acetonide (20)

15 (1.0 g, 2.29 mmol) was reacted with sodium dithionite (2.1 g, 12.0 mmol) and sodium bicarbonate (1.0 g, 12.0 mmol) according to the general procedure above affording 20 (off white powder which was used directly in the next reaction). MS (ESI) m/z calculated for C17H31N3O7S ([M−H]$^-$) 420.19, found 420.1.

2-sulfonatepropionyl-amino(dethia)pantetheine (23)

The deprotection of 20 yielded 23 (off white powder, 800 mg, 2.01 mmol 87.8%, 15→23).

$^1$H NMR (500 MHz, D$_2$O) δ 8.36 (br, 1H, NH), δ 7.99 (br, 1H, NH), 3.92 (s, 1H), 3.75 (q, J=7.0 Hz, 1H), 3.50-3.37 (m, 3H), 3.35-3.19 (m, 5H), 2.43 (t, J=6.6 Hz, 2H), 1.41 (d, J=7.0 Hz, 3H), 0.85 (s, 3H), 0.81 (s, 3H). $^{13}$C NMR (126 MHz, D$_2$O) δ 174.99, 174.07, 170.50, 75.81, 68.45, 61.10, 38.74, 38.69, 35.52, 35.43, 29.26, 20.68, 19.30, 13.02. MS (ESI) m/z calculated for C14H27N3O8S ([M−H]$^-$) 396.15, found 396.1.

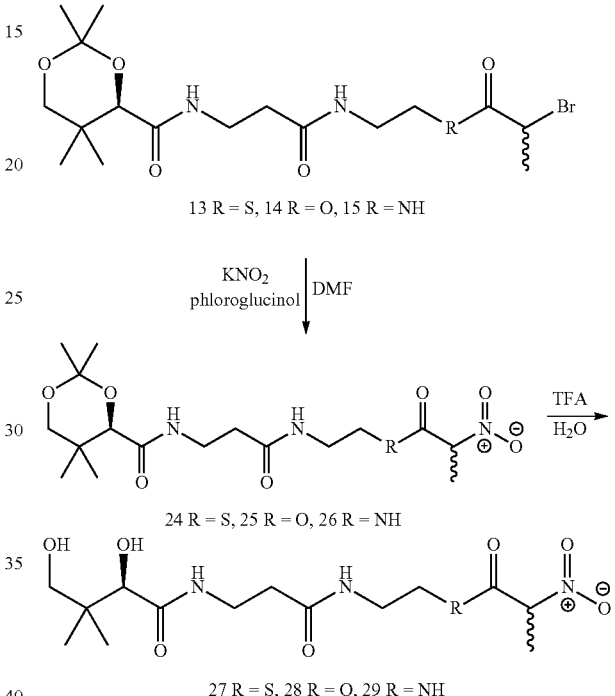

13 R = S, 14 R = O, 15 R = NH

KNO$_2$ phloroglucinol | DMF

24 R = S, 25 R = O, 26 R = NH

TFA / H$_2$O

27 R = S, 28 R = O, 29 R = NH

Preparation of 27-29 Via 24-26 Via 13-15

General Procedure

To a solution of DMF containing 2-bromopropionyl pantetheine acetonide (13-15), anhydrous phloroglucinol and KNO$_3$ were added (Kornblum, N., et al., *J. Am. Chem. Soc.* 1957, 79, 2507-2509). The mixture was allowed to stir for 12 hours at room temperature, over which time a bright yellow-orange color formed. Solvent was removed yielding a yellow oil affording 2-nitropropionyl-pantetheine acetonide (24-26). The acetonides are deprotected with 15% TFA in water. The resulting solution is subjected to preparative HPLC with a gradient of 28→45% of 0.1% TFA in water→methanol or ACN over 30 minutes. Pooled fractions solvent were removed and dissolved in water. The resulting solution is subjected to preparative HPLC with a gradient of 0→35% of 0.1% TFA in water→methanol or ACN over 30 minutes. Pooled fractions solvent were removed and dissolved in water. The solvent is removed affording 2-nitropropionyl-pantetheine (27-29)

2-nitropropionyl-S-pantetheine acetonide (24)

13 (600 mg, 1.32 mmol) was reacted with anhydrous phloroglucinol (441 mg, 3.50 mmol) and KNO$_3$ (255 mg, 3.00 mmol) according to the general procedure above. The solvent was removed and the remaining orange oil was subjected to flash chromatography (0→100% gradient of DCM→acetone or MeOH). Solvent was removed affording 24 (orange oil which was used directly in the next reaction). MS (ESI) m/z calculated for C17H29N3O7S ([M+H]$^+$) 420.17 and ([M−H]$^-$) 418.17, found 420.1, 418.1, respectively.

2-nitropropionyl-S-pantetheine (27)

The deprotection of 24 yielded 27 (light yellow oil, 110 mg, 0.29 mmol 22.0%, 13→27).

$^1$H NMR (500 MHz, D$_2$O) δ 3.85 (s, 1H), 3.42-3.22 (m, 6H), 3.06 (t, J=6.2 Hz, 2H), 2.33 (t, J=6.5 Hz, 2H), 1.65 (s, 3H), 0.79 (s, 3H), 0.75 (s, 3H). $^{13}$C NMR (126 MHz, D$_2$O) δ 194.44, 175.03, 174.04, 75.72, 68.34, 42.24, 38.57, 38.08, 35.33, 35.14, 28.84, 20.44, 19.06, 15.52. MS (ESI) m/z calculated for C14H25N3O7S ([M+H]$^+$) 380.14 and ([M−H]$^-$) 378.14, found 380.2, 378.1, respectively.

2-nitropropionyl-oxa(dethia)pantetheine acetonide (25)

14 (650 mg, 1.49 mmol) was reacted with anhydrous phloroglucinol (188 mg, 1.49 mmol) and KNO$_3$ (254 mg, 2.98 mmol) according to the general procedure above. The solvent was removed and the remaining orange oil was subjected to flash chromatography (0→100% gradient of DCM→acetone or MeOH). Solvent was removed affording 25 (orange oil which was used directly in the next reaction). MS (ESI) m/z calculated for C17H29N3O8 ([M+H]$^+$) 404.20 ([M−H]$^-$) 402.20, found 404.2, 402.1, respectively.

2-nitropropionyl-oxa(dethia)pantetheine (28)

The deprotection of 25 yielded 28 (light yellow oil, 80 mg, 0.22 mmol 14.8%, 14→28).

$^1$H NMR (500 MHz, D$_2$O) δ 4.30-4.13 (m, 2H), 3.86 (s, 1H), 3.38 (m, 5H), 3.26 (d, 1H) 3.08 (q, J=7.3 Hz, 1H), 2.38 (t, J=7.0, 5.8, 3.0 Hz, 2H), 1.16 (t, J=7.3 Hz, 3H), 0.79 (s, 3H), 0.76 (s, 3H). $^{13}$C NMR (126 MHz, D$_2$O) δ 175.06, 174.12, 167.07, 83.58, 75.70, 68.33, 65.40, 46.63, 37.87, 35.37, 35.15, 20.42, 19.01, 8.18. MS (ESI) m/z calculated for C14H25N3O8 ([M+H]$^+$) 364.16 and ([M−H]$^-$) 362.16, found 364.2 and 362.1, respectively.

2-nitropropionyl-amino(dethia)pantetheine acetonide (26)

15 (510 mg, 1.17 mmol) was reacted with anhydrous phloroglucinol (151 mg, 1.20 mmol) and KNO$_3$ (230 mg, 2.70 mmol) according to the general procedure above. The solvent was removed and the remaining orange oil was subjected to flash chromatography (0→100% gradient of DCM→acetone or MeOH). Solvent was removed affording 26 (orange oil which was used directly in the next reaction). MS (ESI) m/z calculated for C17H30N4O7 ([M+H]$^+$) 403.21 and ([M−H]$^-$) 401.21, found 403.2, 401.1, respectively.

2-nitropropionyl-amino(dethia)pantetheine (29)

The deprotection of 26 yielded 29 (light yellow oil, 18.7 mg, 0.05 mmol 4.3%, 15→29).

$^1$H NMR (500 MHz, D$_2$O) δ 5.28 (q, J=6.9, 1.0 Hz, 1H), 3.86 (s, 1H), 3.42-3.34 (m, 3H), 3.33-3.24 (m, 5H), 2.36 (t, J=6.6 Hz, 2H), 1.59 (d, J=6.9, 1.0 Hz, 3H), 0.80 (s, 3H), 0.76 (s, 3H). $^{13}$C NMR (126 MHz, D$_2$O) δ 175.08, 174.15, 167.60, 84.22, 75.74, 68.31, 48.82, 39.02, 38.55, 38.32, 35.26, 20.42, 19.02, 15.04. MS (ESI) m/z calculated for C14H26N4O7 ([M+H]$^+$) 363.18 and ([M−H]$^-$) 361.18, found 363.1, 361.0, respectively.

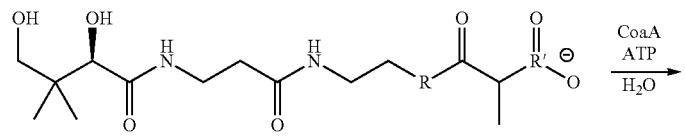

21-23, 27-29
R = S, O, NH
R' = N$^+$, SO

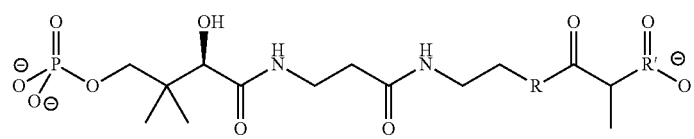

CoaD
CoaE  H$_2$O
ATP

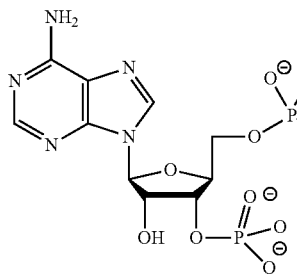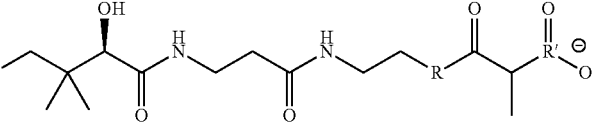

4-9

Chemoenzymatic Preparation of 4-9

General procedure (Strauss, E. et al., *J. Biol. Chem.* 2002, 277, 48205-48209):

A solution containing 100 mM Tris (pH 8.0), 10 mM $MgCl_2$, 50 mM NaCl, 10 mM TCEP (pH 8.0) and 20 μM ATP was used to dissolve the malonyl-pantethine analogs 21-23 or 27-29 at a final concentration of 5.5 mM, ~60-150 mL total. Then CoaA was added to a final concentration of 2.7 μM and the reaction allowed to mix at room temperature for 2 hours. Then CoaD was added to a concentration of 5.6 μM and allowed to mix at room temperature for 1 hour. Then CoaE was added to a final concentration of 13.1 μM and allowed to mix at room temperature overnight. The reaction was quenched with 10% TFA, precipitating the protein out of solution, which was removed by filtration. Reverse phase HPLC was used to purify the final products using a 0→20% gradient of 0.1% TFA in water→methanol or ACN over 30 minutes. Fractions were pooled, rotary evaporated and lyophilized.

2-sulfonatepropionyl-S-CoA (4)

21 (50 mg, 0.12 mmol) was used as starting material to afford 4 (off white powder, 5 mg, 0.01 mmol 8.3%). $^1$H NMR (500 MHz, $D_2O$) δ 8.49 (s, 1H), 8.33 (s, 1H), 6.12 (d, J=5.2 Hz, 1H), 4.83-4.74 (m, 2H), 4.47 (s, 1H), 4.13-4.03 (m, 2H), 3.90 (s, 1H), 3.74 (dd, J=9.7 Hz, 1H), 3.55 (dd, J=9.7 Hz, 1H), 3.40-3.35 (m, 2H), 3.26 (m, 2H), 3.01-2.93 (m, 2H), 2.35 (t, J=6.5, 3.1 Hz, 2H), 1.41 (d, J=7.0 Hz, 3H), 0.85 (s, 3H), 0.79 (s, 3H). $^{13}$C NMR (126 MHz, $D_2O$) δ 197.55, 174.76, 174.05, 149.86, 148.39, 144.56, 142.39, 118.60, 87.80, 74.34, 73.77, 73.72, 71.64, 66.95, 64.29, 38.37, 38.30, 38.24, 35.37, 35.16, 28.48, 20.53, 18.59, 13.38. MS (ESI) m/z calculated for $C_{24}H_{40}N_7O_{20}P_3S_2$ ([M−H]$^-$) 902.10, found 902.2.

2-sulfonatepropionyl-oxa(dethia)CoA (5)

22 (100 mg, 0.25 mmol) was used as starting material to afford 5 (off white powder, 16.7 mg, 0.02 mmol 8.0%). $^1$H NMR (500 MHz, $D_2O$) δ 8.53 (s, 1H), 8.33 (s, 1H), 6.11 (d, J=5.5, 1.9 Hz, 1H), 4.86-4.75 (m, 2H), 4.50 (s, 1H), 4.22-4.07 (m, 4H), 3.89 (s, 1H), 3.87-3.81 (m, 1H), 3.80-3.75 (m, 1H), 3.55-3.51 (m, 1H), 3.41-3.30 (m, 4H), 2.36 (t, J=7.0, 3.4 Hz, 2H), 1.38 (dd, J=7.0, 4.9, 1.6 Hz, 3H), 0.82 (s, 3H), 0.70 (s, 3H). $^{13}$C NMR (126 MHz, $D_2O$) δ 174.67, 174.05, 170.19, 149.84, 148.47, 144.62, 142.49, 118.58, 87.52, 83.19, 74.33, 74.06, 73.70, 72.21, 64.19, 60.49, 52.57, 38.27, 38.08, 35.35, 35.18, 20.72, 18.07, 12.68. MS (ESI) m/z calculated for $C_{24}H_{40}N_7O_{21}P_3S$ ([M−H]$^-$) 886.12, found 886.0.

2-sulfonatepropionyl-amino(dethia)CoA (6)

23 (600 mg, 1.51 mmol) was used as starting material to afford 6 (off white powder, 56.9 mg, 0.06 mmol 4.0%). $^1$H NMR (500 MHz, $D_2O$) δ 8.49 (s, 1H), 8.30 (s, 1H), 6.06 (d, J=5.8 Hz, 1H), 4.83-4.78 (m, 2H), 4.47 (s, 1H), 4.22-4.08 (m, 2H), 3.87 (s, 1H), 3.75 (m, 1H), 3.64 (m, 1H), 3.59-3.50 (m, 2H), 3.33 (m, 4H), 2.37-2.28 (m, 2H), 1.32 (d, J=6.7, 2.8 Hz, 3H), 0.81 (s, 3H), 0.70 (s, 3H). $^{13}$C NMR (126 MHz, $D_2O$) δ 174.65, 174.08, 170.39, 149.74, 148.37, 144.67, 142.39, 118.43, 87.46, 83.15, 74.16, 73.69, 72.18, 65.12, 61.04, 38.60, 38.54, 38.29, 35.40, 35.30, 35.26, 20.68, 18.16, 12.70. MS (ESI) m/z calculated for $C_{24}H_{41}N_8O_{20}P_3S$ ([M−H]$^-$) 885.14, found 885.0.

2-nitropropionyl-S-CoA (7)

27 (110 mg, 0.29 mmol) was used as starting material to afford 7 (off white powder, 63.6 mg, 0.07 mmol 24.1%). $^1$H NMR (500 MHz, $D_2O$) δ 8.48 (s, 1H), 8.30 (s, 1H), 6.06 (d, J=5.9, 1.2 Hz, 1H), 4.81 (t, J=5.1, 2.6 Hz, 1H), 4.75 (t, J=5.7 Hz, 1H), 4.47 (s, 1H), 4.17 (q, J=11.7, 5.9 Hz, 2H), 3.88 (s, 1H), 3.77 (d, J=9.7, 4.3 Hz, 1H), 3.54 (d, J=9.7 Hz 1H), 3.32 (t, J=6.7 Hz, 2H), 3.26 (t, 2H), 3.01 (t, J=6.3 Hz, 2H), 2.30 (t, J=6.6 Hz, 2H), 1.60 (d, J=1.2 Hz, 3H), 0.81 (s, 3H), 0.70 (s, 3H). $^{13}$C NMR (126 MHz, $D_2O$) δ 194.37, 174.61, 174.02, 149.74, 148.37, 144.68, 142.37, 118.42, 87.47, 83.08, 74.43, 74.14, 73.67, 72.23, 65.13, 38.37, 38.31, 38.02, 35.33, 35.17, 28.82, 20.68, 18.29, 15.51. MS (ESI) m/z calculated for $C_{24}H_{39}N_8O_{19}P_3S$ ([M+H]$^+$) 869.13 and ([M−H]$^-$) 867.13, found 869.1, 867.0, respectively.

2-nitropropionyl-oxa(dethia)CoA (8)

28 (80 mg, 0.22 mmol) was used as starting material to afford 8 (off white powder, 46 mg, 0.05 mmol 22.7%). $^1$H NMR (500 MHz, DMSO) δ 8.59 (s, 1H), 8.33 (s, 1H), 8.13 (br, 1H, NH), 7.74 (br, 1H, NH), 5.97-5.83 (m, 1H), 5.65-5.51 (m, 1H), 4.37 (s, 1H), 3.86-3.76 (m, 1H), 3.72 (s, 1H), 3.59-5.46 (m, 1H), 3.35-3.28 (m, 4H), 3.24-3.15 (m, 1H), 2.54-2.43 (m, 2H), 2.32-2.18 (m, 2H), 1.61 (d, J=7.0 Hz, 3H), 0.86 (s, 3H), 0.70 (s, 3H). $^{13}$C NMR (126 MHz, DMSO) δ 173.14, 172.06, 166.27, 150.90, 148.76, 146.28, 141.84, 118.74, 87.51, 83.64, 74.59, 73.89, 73.46, 72.46, 65.38, 39.50, 39.33, 39.17, 37.70, 35.45, 35.23, 21.44, 19.28, 15.64. MS (ESI) m/z calculated for $C_{24}H_{39}N_8O_{20}P_3$ ([M+H]$^+$) 853.15 and ([M−H]$^-$) 851.15, found 853.1, 851.1, respectively.

2-nitropropionyl-amino(dethia)CoA (9)

29 (18.7 mg, 0.05 mmol) was used as starting material to afford 9 (off white powder, 23.1 mg, 0.03 mmol 60%). $^1$H NMR (500 MHz, $D_2O$) δ 8.51 (s, 1H), 8.31 (s, 1H), 6.13-6.04 (m, 1H), 5.32-5.20 (m, 1H), 4.50 (s, 1H), 4.23-4.11 (m, 2H), 3.90 (s, 1H), 3.77 (d, J=9.5, 1H), 3.54 (d, J=9.5, 1H), 3.35 (t, J=6.7 Hz, 2H), 3.28-3.17 (m, 4H), 2.34 (t, J=6.7 Hz, 2H), 1.56 (d, J=6.8 Hz, 3H), 0.83 (s, 3H), 0.72

(s, 3H). $^{13}$C NMR (126 MHz, D$_2$O) δ 174.66, 174.16, 167.57, 149.77, 148.39, 144.67, 142.40, 118.44, 87.47, 84.19, 83.22, 74.20, 73.76, 72.10, 65.10, 39.03, 38.35, 38.29, 38.26, 35.38, 35.31, 20.68, 18.31, 15.05. MS (ESI) m/z calculated for C24H40N9O19P3 ([M+H]$^+$) 852.17 and ([M−H]$^−$) 850.17, found 852.7 and 852.6, respectively.

IV. Extinction Coefficient Determination

The extinction coefficients of 4-6 were assumed to be the same as acetyl-CoA (15.4 mM$^{-1}$cm$^{-1}$ at A259), as there was no appreciable absorption at 259 nm for the intermediates 18-23. The nitro bearing analog intermediates 24-29 have an absorption with a peak at 318 and 326 nm with some absorption at 259 nm due to the tail of the 318 peak in 10 mM potassium phosphate buffer (KH$_2$PO$_4$/K$_2$HPO$_4$) at pH 6.5. Calculation of an extinction coefficient was performed at 259 nm for 27 and use to adjust the extinction coefficient of 7-9. Compound 27 was measured to 5.0379 mg and dissolved in 1 mL of water (100 mM) buffered to pH 7.0 with Tris:HCl. Measurement of the UV spectrum for a serial dilution of 27 gave an extinction coefficient at 259 nm of 0.997±0.022 mM$^{-1}$cm$^{-1}$. Addition of the adenine and nitro extinction coefficients yields overall extinction coefficients at 259 nm for 7, 8 and 9 of 16.4 mM$^{-1}$cm$^{-1}$.

V. Cloning of coaA, coaD, coaE and ygfG from *Escherichia coli*

The pBS3080 expression plasmid was used to generate gene fusions with N-terminal hexahistidine tags (His-tag) and Tobacco etch virus protease (TEV) sites as previously described (Lohman, J R, et al., *Biochemistry* 2013, 52(5), 902-911). Briefly, pBS3080 was digested with BsmFI and purified by gel electrophoresis and the linearized vector was treated with T4 DNA polymerase in the presence of dGTP at 20° C. for 30 min and then heated at 75° C. for 20 min to denature the polymerase, affording overhangs with complementary sequences to clone the PCR-amplified genes. The coaA/D/E and ygfG genes were amplified by PCR from *E. coli* DH5a genomic DNA. The PCR products were purified by gel electrophoresis, and similarly treated with T4 DNA polymerase in the presence of dCTP at 20° C. for 30 min and then heated at 75° C. The T4 DNA polymerase-treated pBS3080 vector and gene fragments were then mixed at room temperature, annealed on ice for 5 min, and transformed into *E. coli* DH5a. Plasmids containing the appropriate genes were isolated and confirmed by DNA sequencing, yielding expression plasmids for CoaA (pJLHis6T-ecCoaA), CoaD (pJLHis6T-ecCoaD), CoaE (pJLHis6T-ecCoaE) and MMCD-His6 (pJLHis6T-ecYgfG).

VI. Expression and Purification of CoaA, CoaD, CoaE and YgfG (MMCD)

CoaA (pJLHis6T-ecCoaA), CoaD (pJLHis6T-ecCoaD), CoaE (pJLHis6T-ecCoaE) and MMCD (pJLHis6T-ecYgfG) were transformed into *E. coli* BL21 (DE3), and the resultant recombinant strains were grown overnight in 50 mL of LB and 50 µg/mL kanamycin. A 5 mL aliquot of the overnight culture was used to inoculate 1 L of LB containing 10 mM MgCl$_2$ and 50 50 µg/mL kanamycin, which was incubated at 37° C. while being shaken at 180 rpm. Once the OD$_{600}$ reached ~0.5-0.6, the temperature was reduced to 18° C. Once the cultures reached thermal equilibrium, gene expression was induced by the addition of isopropyl β-d-thiogalactopyranoside with a final concentration of 500 µg/mL, with incubation for an additional 16 hours. *E. coli* cells were harvested by centrifugation at 6300 rpm and 4° C. for 30 min.

*E. coli* cell pellets, carrying CoaA, CoaD, CoaE and MMCD were re-suspended in lysis buffer [1 µg/mL DNase, 300 mM NaCl, 20 mM imidazole, 10% glycerol, and 20 mM Tris-HCl (pH 8.0)], sonicated (60×1 s on ice), and clarified by centrifugation at 11000 rpm and 4° C. for 30 min. The supernatant was filtered applied to a 5 mL HisTrap HP (GE Healthcare,) and washed with lysis buffer using an Äkta pure fast-performance liquid chromatography system (GE Healthcare,). Wash buffer [300 mM NaCl, 40 mM imidazole and 20 mM Tris-HCl (pH 8.0)] was used to remove additional contaminants, and proteins were eluted with wash buffer containing 500 mM imidazole. At this point the purity of CoaA, CoaD and CoaE from the fractions was analyzed by sodium dodecyl sulfate-polyacrylamide gel electrophoresis (SDS-PAGE). Pure fractions were pooled, concentrated, buffer-exchanged into 10 mM Tris-HCl (pH 8.0) and 200 mM NaCl, frozen in small aliquots with liquid nitrogen, and stored at −80° C. MMCD-His6 was buffer-exchanged into 10 mM Tris-HCl (pH 8.0) and 200 mM NaCl and further purified using size exclusion chromatography HiLoad 26/600 Superdex 200 pg (GE Healthcare) in the same buffer. The purity of the protein from the fractions was analyzed by SDS-PAGE. Pure fractions were pooled, concentrated via filtration and final concentration determined using calculated extinction coefficients at 280 nm. The proteins were frozen in small aliquots with liquid nitrogen, and stored at −80° C.

MMCD(S2A) expressed from pJL-ecYgfG(S2A) was subjected to similar cell lysis, sonication, and clarity by centrifugation as above. The supernatant was slowly mixed with 15% w/v ammonium sulfate for 30 minutes at 4° C. The sample was clarified by centrifugation at 11000 rpm and 4° C. for 30 min. The supernatant was slowly mixed with an additional 20% w/v (35% w/v total) ammonium sulfate for 30 minutes at 4° C. The sample was clarified by centrifugation at 11000 rpm and 4° C. for 30 min. The supernatant was filtered, buffer-exchanged into 10 mM Tris-HCl (pH 8.0) and 200 mM NaCl and loaded onto a 5 mL HiTrap Q HP (GE Healthcare,). A linear gradient over 12 column volumes from 0 to 70% buffer B [50 mM Tris-HCl (pH 8.5) and 1.0 M NaCl] was used to elute the proteins. The pooled fractions were buffer-exchanged into 10 mM Tris-HCl (pH 8.0) and 200 mM NaCl and further purified using size exclusion chromatography HiLoad 26/600 Superdex 200 pg (GE Healthcare). The purity of the protein from the fractions was analyzed by SDS-PAGE. Pure fractions were pooled, concentrated via filtration and final concentration determined using calculated extinction coefficients at 280 nm. The protein was frozen in small aliquots with liquid nitrogen, and stored at −80° C.

VII. Crystallization, X-ray Crystallographic Collection and Refinement of MMCD

MMCD(S2A) was screened against 384 crystallization conditions in 500 nL sitting drops at 20° C., set up with a Mosquito (TTPlabtech, Melbourne, Australia) to find initial conditions. MMCD(S2A) [23 mg/mL in 10 mM Tris-HCl (pH 8.0) and 200 mM NaCl], 10 mM 4-9 and 10 µM NiSO$_4$(H$_2$O)$_6$ (Ni omitted in solution with compound 5) were screened by the hanging drop method over 1.0 mL wells containing 0-5% PEG 400, 50-200 mM NaCl, 0.4 M NaH$_2$PO$_4$/1.6 M K$_2$HPO$_4$, and 0.1 M imidazole (pH 8.0) in 4 µL drops (1:1, protein:well and 3:1, protein:well), which produced crystals in conditions with less than or equal to 4% PEG 400.

Crystals were looped and frozen directly out of the drops with liquid nitrogen. X-ray diffraction data for all datasets were collected at Advanced Photon Source LS-CAT beamline 21-ID-G (PDB: 6N92, 6N93, and 6N94) at a wavelength of 0.97856, beamline 21-ID-F (PDB: 6N95 and 6N97) at a wavelength 0.97872, and beamline 21-ID-D (PDB: 6N96) at a wavelength 0.97849. Diffraction intensities were integrated, reduced, and scaled using HKL2000, with data collection and refinement statistics listed in Table 1. Molecular replacement with the program Phaser was used to phase our initial structure of MMCD with 7 (PDB: 6N92) based off PDB 1EF8 coordinates. The remaining structures of MMCD with 4-6 (PDB: 6N95, 6N96, and 6N97) and 8-9 (PDB: 6N93 and 6N94) were solved by isomorphous replacement from 7 (PDB: 6N92). Refinement was conducted using Refmac in the CCP4i package with automated model building performed with ARP/wARP and manual model building with Coot (Lu J, et al., *Protein Engineering, Design & Selection: PEDS* 2017, 30(5), 395-399; Heath, R J, et al., *Natural Product Reports* 2002, 19(5), 581-596).

VIII. MMCD Enzymatic Assays, pH Rate Profile and $K_i$ Determination

General procedure for MMCD-His6 catalyzed activity assays. The reactions were performed in a 550 µL reaction mixture which contained 50 mM potassium phosphate buffer ($KH_2PO_4/K_2HPO_4$) at pH 6.5 unless otherwise noted, 10 mM $MgCl_2$, methylmalonyl-CoA and the assay was initiated by the addition of MMCD. Reaction mixtures were incubated at 25° C., 65 µL aliquots taken at times noted below were quenched with 25 µL of 50% TFA v/v, precipitating the protein. Centrifugation at 2000 rpm at 25° C. for 10 minutes was used to pellet the protein and the supernatant was analyzed via the procedure outlined below.

General procedure for determination of methylmalonyl-CoA, propionyl-CoA and CoA concentrations in MMCD catalyzed assays. Substrate and product concentrations were determined using HPLC with detection at $A_{254}$ over the 250×4.6 mm C18(2) column. The analytes were separated with a 2→25% gradient of 0.1% TFA in water→ACN over 20 min. Peak areas of substrate and products were converted to concentration by summing their areas and dividing each peak by this total to give relative percentages that were converted to concentration by adjusting to the starting concentration of methylmalonyl-CoA. This procedure gave essentially the same values as using a standard curve to generate concentrations for each peak, but enhanced reproducibility due to small differences in recovery from the reaction quenching step outlined above.

The pH rate profile was performed according to the general procedure above with 50 mM potassium phosphate buffer ($KH_2PO_4/K_2HPO_4$) at pH 4.5, 5.0, 5.5, 6.0, 6.5, 7.0, 7.5, 8.0, 8.5, 9.0, and 9.5, 500 µM methylmalonyl-CoA, and reactions were initiated by the addition of 5 nM MMCD. Aliquots were taken at the times 30s, 50s, 70s, 100s, 130s, 190s, 310s, and 910s.

Inhibition assays of MMCD by 4-9 were performed according to the general procedure above with 200 µM methylmalonyl-CoA, 4-9 (0 µM, 2 µM, 5 µM, 20 µM, and 50 µM) and the assay was initiated by the addition of 1 nM MMCD. Aliquots were taken at the times 20s, 40s, 60s, 150s, 300s, 600s, 900s, and 1800s.

The initial rates ($V_i$) of decomposition of methylmalonyl-CoA were determined by fitting the progress curve data to equation (1) which describes a simple exponential decay with rate (k), time (t) and initial substrate concentration ($[S]_t$). The rate of formation of propionyl-CoA or CoA could be fit to equation (2). The derivative at time 0 for Equation (1) divided by enzyme concentration gives the initial rates $V_i$ as shown in equation (3). Using this method rather than linear estimation from the early data points gave similar values. However, it allowed more accurate determination of $V_i$ at early time points.

$$[S]=[S]_t \cdot e^{-k \cdot t} \qquad \text{Equation (1)}$$

$$[S]=[S]_t \cdot (1-e^{k \cdot t}) \qquad \text{Equation (2)}$$

$$V_i=([S]_t \cdot k)/[E] \qquad \text{Equation (3)}$$

Initial rate data for the pH rate profile was fit to equation (4) to determine the $pK_a$ of a single titratable group for the decomposition of methylmalonyl-CoA and appearance of propionyl-CoA. Equation (5) describes two titratable groups and was used to fit appearance of CoA.

$$V_i = \frac{V_{max}}{1 + 10^{pH-pK_a}} \qquad \text{Equation (4)}$$

$$V_i = \frac{V_{max}}{(1 + 10^{pK_{a1}-pH} + 10^{pH-pK_{a2}})} \qquad \text{Equation (5)}$$

Inhibition of MMCD by 4-9 was determined by fitting initial rate data to equation (6), which describes competitive inhibition and $V_{ii}$ describes the $V_i$ in the presence of inhibitor (Lu, J, et al., *Protein Eng. Des. Sel.* 2017, 30, 395-399). The values of $(V_i \cdot V_{is})/(V_{ii}-V_{is})$ and $K_m/k_{cat}$ were determined from the initial slopes of $V_i$ or $V_{ii}$ versus substrate concentration rather than from the full assay, see Figures S5 and S9. A minimum of two concentrations were used, 20 or 50 µM of each 4-9 and the experiments were repeated at least twice.

$$K_i = \frac{V_{ii} \cdot V_{is}}{V_{ii} - V_{is}} \cdot \frac{[I]}{[E] \cdot [S]} \cdot \frac{K_m}{k_{cat}} \qquad \text{Equation (6)}$$

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alterna-

What is claimed is:

1. A compound having a formula

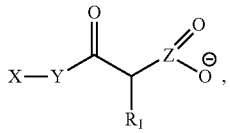
(I)

or a pharmaceutically acceptable salt, hydrate, or solvate thereof, wherein

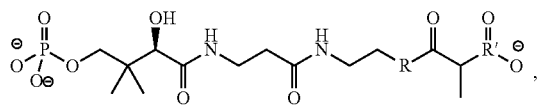

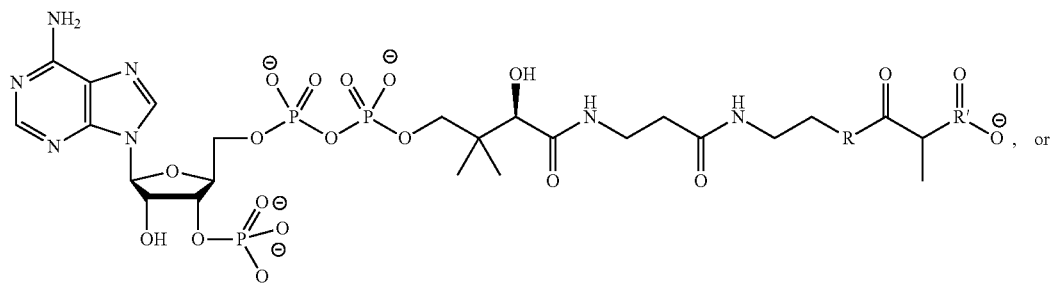

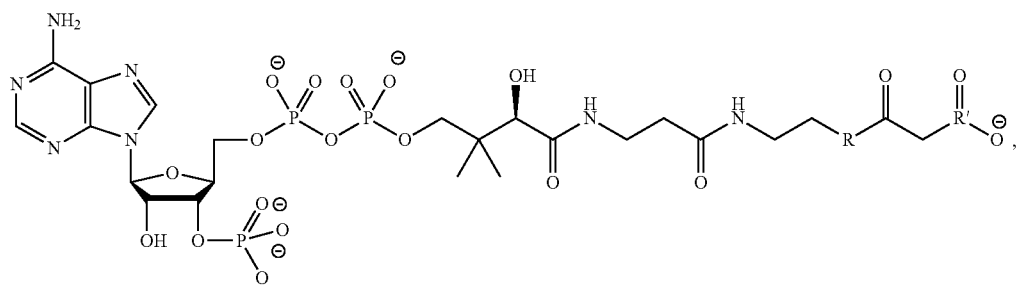

X is co-enzyme A (CoA) or

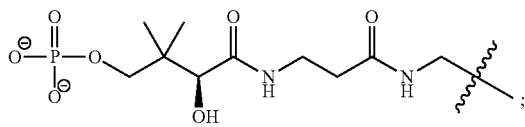 [SMILES: *CNC(=O)CCNC(=O)[C@@H](O)C(C)(C)COP(=O)([O-])[O-]]

Y is methylene (—CH$_2$—), S, SO, NH, or O;
Z is N, S or SO; and
R$^1$ is hydrogen, an alkyl, alkenyl, or alkynyl.

2. The compound according to claim 1, wherein R$_1$ is hydrogen, or a C$_1$-C$_{24}$ alkyl.

3. The compound according to claim 2, wherein R$_1$ is hydrogen.

4. The compound according to claim 2, wherein R$_1$ is a C$_1$-C$_{24}$ alkyl.

5. The compound according to claim 4, wherein R$_1$ is methyl.

6. The compound according to claim 1, wherein X is coenzyme A (CoA).

7. The compound according to claim 1, wherein X is

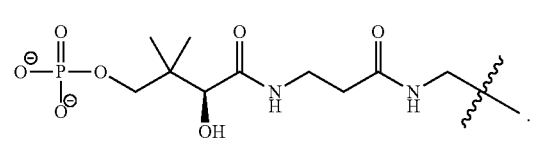 [SMILES: *CNC(=O)CCNC(=O)[C@@H](O)C(C)(C)COP(=O)([O-])[O-]]

8. The compound according to claim 1, wherein said compound is

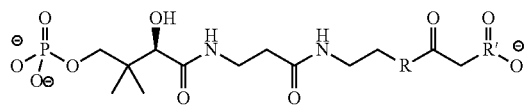

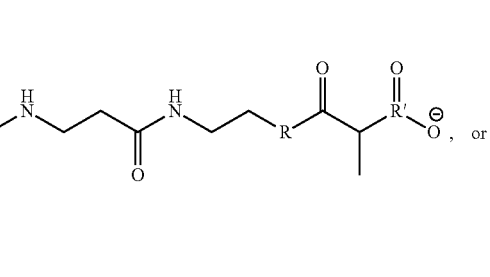

wherein R=S, O, NH; R'=SO, N$^+$.

9. A pharmaceutical composition comprising one or more compounds of claim 1, or a pharmaceutically acceptable salt thereof, together with one or more diluents, excipients or carriers.

10. A pharmaceutical composition comprising one or more compounds of claim 1, or a pharmaceutically acceptable salt thereof, in combination with one or more other compounds of the same of different mode of action, together with one or more diluents, excipients or carriers.

* * * * *